(12) United States Patent
Camacho Gomez et al.

(10) Patent No.: US 8,796,284 B2
(45) Date of Patent: Aug. 5, 2014

(54) 4-AMINOPYRIMIDINE DERIVATIVES AND THEIR AS AS ADENOSINE $A_{2a}$ RECEPTOR ANTAGONISTS

(75) Inventors: Juan Alberto Camacho Gomez, Barcelona (ES); Julio Cesar Castro-Palomino Laria, Barcelona (ES)

(73) Assignee: Palobiofarma, S.L., Barcelona (ES)

( * ) Notice: Subject to any disclaimer, the term of this patent is extended or adjusted under 35 U.S.C. 154(b) by 0 days.

(21) Appl. No.: 13/636,624

(22) PCT Filed: Mar. 29, 2011

(86) PCT No.: PCT/IB2011/000664
§ 371 (c)(1),
(2), (4) Date: Oct. 18, 2012

(87) PCT Pub. No.: WO2011/121418
PCT Pub. Date: Oct. 6, 2011

(65) Prior Publication Data
US 2013/0053308 A1    Feb. 28, 2013

(30) Foreign Application Priority Data

Mar. 31, 2010  (ES) .................................. 201030489

(51) Int. Cl.
*A01N 43/54*    (2006.01)
*C07D 239/42*    (2006.01)
*C07D 401/04*    (2006.01)

(52) U.S. Cl.
USPC ........................... 514/256; 544/295; 544/326

(58) Field of Classification Search
USPC ................... 544/328, 295; 514/256
See application file for complete search history.

(56) References Cited

U.S. PATENT DOCUMENTS 6,586,441 B2 *   7/2003   Borroni et al. ................ 514/275

FOREIGN PATENT DOCUMENTS

| WO | WO 2005/058883 | 6/2005 |
| WO | WO 2008/110891 | 9/2008 |
| WO | WO 2008/116185 | 9/2008 |

OTHER PUBLICATIONS

Masquelin et al. A Novel Solution- and Solid-Phase Approach to 2,4,5-Tri- and 2,4,5,6-Tetrasubstituted Pyrimidines and Their Conversion into Condensed Heterocycles. Helvetica Chimica Acta. (1998). vol. 81: p. 646-660.*
V. Katritch et al., 53 Journal of Medicinal Chemistry, 1799-1809 (2010).*
L. Yu et al., 63 Annals of Neurology, 338-346 (2008).*
C. E. Muller et al., Biochimica et Biophysica Acta, 1290-1308 (2011).*
J.H. Poupaert, Drug Design: Basic Principles and Applications, in 2 Encyclopedia of Pharmaceutical Technology 1362-1369, 1367 (James Swarbrick ed., 3rd ed., 2007).*
B.A. Chabner et al., Chemotherapy of Neoplastic Diseases, Neoplastic Agents in, Goodman & Gilman's: The Pharmacological Basis of Therapeutics 1315-1403, 1315 (L.L. Brunton et al., eds., 11th ed., 2006).*
G.W. Kenner et al., Journal of the Chemical Society, 388-390 (1943).*
B. Decroix et al., Journal of Chemical Research, Synopses 132-133 (1978).*

* cited by examiner

*Primary Examiner* — Deepak Rao
*Assistant Examiner* — Alexander R Pagano
(74) *Attorney, Agent, or Firm* — Leason Ellis LLP

(57) ABSTRACT

New 4-amino-pyrimidine derivatives as potent antagonists of the adenosine $A_{2a}$ receptor formula (I): (I) The invention provides as well a method for preparing such compounds, pharmaceutical compositions comprising an effective amount of these compounds and the use of such compounds in the manufacture of a medicament to treat pathological affections that can be improved by antagonism of the adenosine $A_{2a}$ receptor.

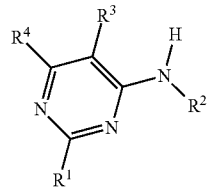

11 Claims, No Drawings

4-AMINOPYRIMIDINE DERIVATIVES AND THEIR AS AS ADENOSINE $A_{2a}$ RECEPTOR ANTAGONISTS

FIELD OF THE INVENTION

The present invention relates to new pyrimidine derivatives conveniently substituted as antagonists of the adenosine $A_{2a}$ receptor. Other objectives of the present invention are to provide a method for preparing such compounds, pharmaceutical compositions comprising an effective amount of these compounds, the use of compounds in the manufacture of a medicament to treat pathological affections or diseases that can be improved by antagonism of the adenosine $A_{2a}$ receptor.

BACKGROUND OF THE INVENTION

The effects of adenosine are mediated through at least four specific cell membrane receptors so far identified and classified as receptors $A_1$, $A_{2A}$, $A_{2B}$ and $A_3$ belonging to the G protein-coupled receptor family. The $A_1$ and $A_3$ receptors down-regulate cellular cAMP levels through their coupling to $G_i$ proteins, which inhibit adenylate cyclase. In contrast, $A_{2A}$ and $A_{2B}$ receptors couple to $G_s$ proteins that activate adenylate cyclase and increase intracellular levels of cAMP. Through these receptors, adenosine regulates a wide range of physiological functions.

Several preclinical studies demonstrate the usefulness of adenosine $A_{2A}$ receptor antagonists to treat neurodegenerative diseases, mainly Parkinson's, Huntington's or Alzheimer's diseases (*Trends in Neurosci.* 2006, 29(11), 647-654; *Expert Opinion Ther. Patents*, 2007, 17, 979-991; *Exp. Neurol.* 2003, 184(1), 285-284; *Prog. Brain Res*, 2010, 183, 183-208; *J. Alzheimer Dis.* 2010, Suppl 1, 117-126; *J. Neurosci.* 2009, 29(47), 14741-14751; *Neuroscience*, 2010, 166(2), 590-603; *J. Pharmacol. Exp. Ther.* 2009, 330(1), 294-303; *Frontiers Biosci.* 2008, 13, 2614-2632).

Besides the welcome utility of $A_{2A}$ receptor antagonists to treat neurodegenerative diseases, those compounds have been considered for complementary symptomatic indications. These are based on the evidence that $A_{2A}$ receptor activation may contribute to the pathophysiology of a range of neuropsychiatric disorders and dysfunctions such as depression, excessive daytime sleepiness, restless legs syndrome, attention deficit hyperactivity disorder, and cognitive fatigue (*Neurology*, 2003, 61(11 Suppl 6), S82-S87; *Behav. Pharmacol.* 2009, 20(2), 134-145; *CNS Drug Discov.* 2007, 2(1), 1-21).

Some authors suggest the application of $A_2$ antagonists for the treatment of diabetes (WO1999035147; WO2001002400).

Other studies suggest the involvement of $A_{2a}$ adenosine receptors in wound healing or atrial fibrillation (*Am J Path*, 2007, 6, 1774-1778; *Arthritis & Rheumatism*, 2006, 54(8), 2632-2642).

For this reason, there is an increasing interest in the discovery of novel, potent and selective adenosine $A_{2a}$ antagonists. Some of the potent adenosine $A_{2a}$ antagonists discovered in the past by the pharmaceutical companies, have advanced into clinical trials showing positive results and demonstrating the potential of this compound class for the treatment of neurodegenerative disorders like Parkinson's, Huntington's or Alzheimer's disease, but also in other CNS related diseases like depression, restless syndrome, sleep and anxiety disorders (*Clin. Neuropharmacol.* 2010, 33, 55-60; *J. Neurosci.* 2010, 30(48), 16284-16292; *Parkinsonisn Relat. Disord.* 2010, 16(6), 423-426; 1 *Expert Opinion Ther. Patents*, 2010, 20(8), 987-1005; *Current Opinion in Drug Discovery & Development*, 2010, 13(4), 466-480 and references therein; *Mov. Disorders*, 2010, 25(2), S305).

The present invention relates to novel 4-amino-pyrimidine derivatives as potent antagonists of the adenosine $A_{2a}$ receptor. There are reports in the literature showing that 4-aminopyrimidines of formula:

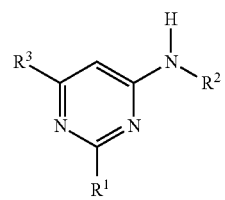

Wherein $R^1$ and $R^3$ can be heteroaryl groups and $R^2$ can be a hydrogen atom or a substituted alkyl chain are potent adenosine $A_{2a}$ receptor antagonists (e.g. WO 2005058883 A1; WO2008116185).

However, we surprisingly found that by introducing an electron-withdrawing substituent at the position 5 of the pyrimidine-ring the potency of the compounds as adenosine $A_{2a}$ antagonists can be considerably increased in comparison to the parent unsubstituted derivatives, as illustrated by the following examples:

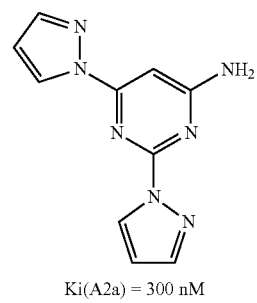

Ki(A2a) = 300 nM

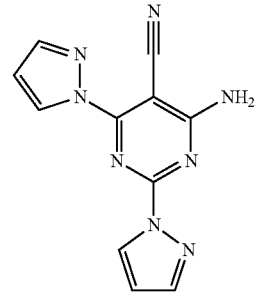

Ki(A2a) = 6 nM (Example 48)

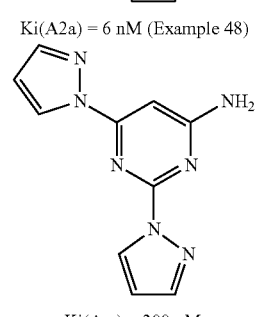

Ki(A2a) = 300 nM

-continued

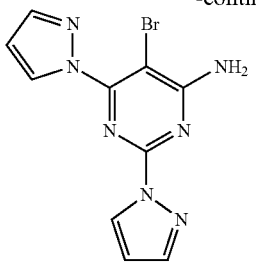

Ki(A$_{2a}$) = 12 nM (Example 1)

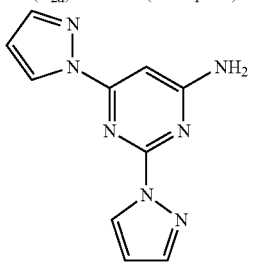

Ki(A$_{2a}$) = 300 nM

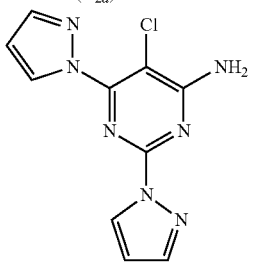

Ki(A$_{2a}$) = 15 nM (Example 46)

DETAILED DESCRIPTION OF THE INVENTION

The present invention relates to new pyrimidine derivatives of formula (I):

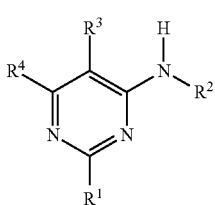

(I)

Wherein:
R$^1$ represents a five-membered heteroaryl ring optionally substituted by one or more selected substituents of the group consisting of halogen, lower alkyl, cycloalkyl, lower alkoxy or cyano
R$^2$ represents independently:
a) a hydrogen atom
b) an alkyl or cycloalkyl group, which is optionally substituted by one or more halogen atoms or by one or more cycloalkyl, hydroxyl or alkoxy groups
R$^3$ represents independently:
a) an halogen atom
b) a cyano group
c) a trifluoromethyl group
d) a cyclopropyl or cyclobutyl group
e) a five-membered heteroaryl group optionally substituted by one or more halogen atoms or by one or more groups like alkyl, cycloalkyl, alkoxy, amino, mono- or dialkylamino
R$^4$ represents independently:
a) a five-membered heteroaryl group optionally substituted by one or more halogen atoms or by one or more groups like alkyl, cycloalkyl, alkoxy, amino, mono- or dialkylamino, alkoxyalkyl
b) a group N(R$^5$)(R$^6$) in which R$^5$ and R$^6$ represent independently:
a hydrogen atom
an alkyl or cycloalkyl group, linear or branched, optionally substituted by one or more halogen atoms or by one or more groups like cycloalkyl, alkoxy, amino, mono- or dialkylamino
R$^5$ and R$^6$ form together with the nitrogen atom to that they are attached a saturated heterocyclic group of 4 to 6 members in which further heteroatom may be inserted, which is optionally substituted by one or more halogen atoms
c) a group —OR$^7$ or —SR$^7$, where R$^7$ represents independently:
an alkyl or cycloalkyl group, linear or branched, optionally substituted by one or more halogen atoms or by one or more groups like cycloalkyl, alkoxy, amino, mono- or dialkylamino
a Phenyl ring optionally substituted with one or more halogen atoms Other aspects of the present invention are: a) pharmaceutically acceptable salts of such compounds, b) pharmaceutical compositions comprising an effective amount of said compounds, c) the use of such compounds in the manufacture of a medicament for treating diseases that can be improved by antagonism of an adenosine receptor, d) procedures for the treatment of diseases that can be improved by antagonism of an adenosine receptor comprising such procedures of the administration of these compounds of the invention to a subject requiring such treatment, and e) the combination of such compounds with other drugs used for the treatment of diseases conditions that can be improved by antagonism of an adenosine receptor.

As used herein the term lower alkyl embraces optionally substituted, linear or branched radicals having 1 to 8, preferably 1 to 6 and more preferably 1 to 4 carbon atoms.

Examples include methyl, ethyl, n-propyl, i-propyl, n-butyl, sec-butyl and tert-butyl, n-pentyl, 1-methylbutyl, 2-methylbutyl, isopentyl, 1-ethylpropyl, 1,1-dimethylpropyl, 1,2-dimethylpropyl, n-hexyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 2-methylpentyl, 3-methylpentyl, and iso-hexyl radicals.

As used herein, the term lower alkoxy embraces optionally substituted, linear or branched oxy-containing radicals each having alkyl portions of 1 to 8, preferably 1 to 6 and more preferably 1 to 4 carbon atoms.

Preferred alkoxy radicals include methoxy, ethoxy, n-propoxy, i-propoxy, n-butoxy, sec-butoxy, t-butoxy, trifluoromethoxy, difluoromethoxy, hydroxymethoxy, 2-hydroxyethoxy or 2-hydroxypropoxy.

As used herein, the term lower alkylthio embraces optionally substituted, linear or branched thio-containing radicals each having alkyl portions of 1 to 8, preferably 1 to 6 and more preferably 1 to 4 carbon atoms.

Preferred alkylthio radicals include methylthio, ethylthio, n-propylthio, i-propylthio, n-butylthio, sec-butylthio, t-butylthio, trifluoromethylthio, difluoromethylthio, hydroxymethylthio, 2-hydroxyiethylthio or 2-hydroxypropylthio.

As used herein, the term cyclic group embraces, unless otherwise specified, carbocyclic and heterocyclic radicals. The cyclic radicals can contain one or more rings. Carbocyclic radicals may be aromatic or alicyclic, for example cycloalkyl radicals. Heterocyclic radicals also include heteroaryl radicals.

As used herein, the term aromatic group includes, typically, an aromatic ring system of 5 to 14 members, such as a ring of 5 or 6 members which may contain one or more heteroatoms selected from O, S, and N. When there are no heteroatoms present, the radical is denominated aryl radical, when there are present at least one heteroatom, it is denominated heteroaryl radical. The aromatic radical can be monocyclic or polycyclic, such as phenyl or naphthyl. When an aromatic radical or moiety carries 2 or more substituents, the substituents may be the same or different.

As used herein, the term five-membered heteroaryl ring embraces typically a 5-membered ring system comprising at least one heteroaromatic ring and containing at least one heteroatom selected from O, S, and N.

Examples include furyl, oxadiazolyl, oxazolyl, imidazolyl, thiazolyl, thiadiazolyl, thienyl, pyrrolyl, triazolyl, imidazolidinyl, and pyrazolyl radicals. The preferred radicals are pyrazolyl, triazolyl, thiazolyl, and furyl optionally substituted.

When a heteroaryl radical carries 2 or more substituents, the substituents may be the same or different.

As used herein, some of the atoms, radicals, moieties, chains or cycles present in the general structures of the invention are "optionally substituted". This means that these atoms, radicals, moieties, chains or cycles can be either unsubstituted or substituted in any position by one or more, for example 1, 2, 3 or 4, substituents, whereby the hydrogen atoms bound to the unsubstituted atoms, radicals, moieties, chains or cycles are replaced by chemically acceptable atoms, radicals, moieties, chains or cycles. When two or more substituents are present, each substituent may be the same or different.

As used herein, the term halogen atom embraces chlorine, fluorine, bromine or iodine atoms typically a fluorine, chlorine or bromine atom, most preferably chlorine or fluorine. The term halo when used as a prefix has the same meaning.

As used herein, the term pharmaceutically acceptable salt embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

Other preferred salts according to the invention are quaternary ammonium compounds wherein an equivalent of an anion (X—) is associated with the positive charge of the N atom. X— may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. X— is preferably an anion selected from chloride, bromide, iodide, sulphate, nitrate, acetate, maleate, oxalate, succinate or trifluoroacetate. More preferably X— is chloride, bromide, trifluoroacetate or methanesulphonate.

According to one embodiment of the present invention in the compounds of formula (I), $R^1$ represents independently an optionally substituted pyrazole, triazole, thiazole or thiophene rings According to a preferred embodiment of the present invention in the compounds of formula (I), $R^1$ represents independently an optionally substituted pyrazole, triazole, or thiazole and $R^2$ represents a hydrogen atom According to more preferred embodiment of the present invention in the compounds of formula (I), $R^1$ represents independently an optionally substituted pyrazole, triazole, or thiazole rings and $R^2$ represents a hydrogen atom and $R^3$ represents a bromine atom, a cyano group or a trifluoromethyl group According to more preferred embodiment of the present invention in the compounds of formula (I), $R^1$ and $R^4$ represents independently an optionally substituted pyrazole, triazole, thiazole or thiophene rings and $R^2$ represents a hydrogen atom and $R^3$ represents a bromine atom, a cyano group or a trifluoromethyl group According to an even more preferred embodiment of the present invention in the compounds of formula (I), $R^1$ and $R^4$ represent a pyrazole ring optionally substituted by one or more substituents, the group $R^2$ represents a hydrogen atom and the group $R^3$ represents a bromine atom, a cyano group or a trifluoromethyl group According to other preferred embodiment of the present invention in the compounds of formula (I), $R^1$ represents an optionally substituted pyrazole, thiazole or triazole rings, $R^2$ represents a hydrogen atom $R^3$ represents a bromine atom and $R^4$ represents independently a group —N($R^5$)($R^6$), in which $R^5$ represents a hydrogen atom and $R^6$ represents an alkyl group optionally substituted by fluorine atoms, amino, dialkylamino and alkoxy.

According to other preferred embodiment of the present invention in the compounds of formula (I), $R^1$ represents an optionally substituted pyrazole ring, $R^2$ represents a hydrogen atom $R^3$ represents a bromine atom and $R^4$ represents independently an isopropyl, cyclopropyl and cyclobutyl rings optionally substituted by fluorine atoms According to other preferred embodiment of the present invention in the compounds of formula (I), $R^1$ represents an optionally substituted pyrazole ring, $R^2$ represents a hydrogen atom $R^3$ represents a bromine atom and $R^4$ represents independently an oxygen or sulphur atoms optionally substituted.

Particular individual compounds of the invention include:
5-bromo-6-isopropyl-2-(1H-pyrazol-1-yl)pyrimidin-4-amine
5-bromo-2,6-di-(1H-pyrazol-1-yl)pyrimidin-4-amine
5-bromo-6-cyclopropyl-2-(1H-pyrazol-1-yl)pyrimidin-4-amine
5-bromo-6-(4-methyl-1H-pyrazol-1-yl)-2-(1H-pyrazol-1-yl)pyrimidin-4-amine
5-bromo-2-(1H-pyrazol-1-yl)-6-(pyrrolidin-1-yl)pyrimidin-4-amine
5-bromo-$N^4$-cyclopentyl-2-(1H-pyrazol-1-yl)pyrimidin-4,6-diamine
5-bromo-6-(piperidin-1-yl)-2-(1H-pyrazol-1-yl)pyrimidin-4-amine
5-bromo-6-morpholino-2-(1H-pyrazol-1-yl)pyrimidin-4-amine
5-bromo-6-(4-methylpiperazin-1-yl)-2-(1H-pyrazol-1-yl)pyrimidin-4-amine 5-bromo-N⁴-cyclopropyl-2-(1H-pyrazol-1-yl)pyrimidine-4,6-diamine
6-(azetidin-1-yl)-5-bromo-2-(1H-pyrazol-1-yl)pyrimidin-4-amine
5-bromo-N⁴-cyclobutyl-2-(1H-pyrazol-1-yl)pyrimidine-4,6-diamine
5-bromo-6-(2-methylpyrrolidin-1-yl)-2-(1H-pyrazol-1-yl)pyrimidin-4-amine
5-bromo-6-((R)-2-methylpyrrolidin-1-yl)-2-(1H-pyrazol-1-yl)pyrimidin-4-amine
5-bromo-N⁴,N⁴-dimethyl-2-(1H-pyrazol-1-yl)pyrimidin-4,6-diamine
5-bromo-N⁴,N⁴-diethyl-2-(1H-pyrazol-1-yl)pyrimidin-4,6-diamine
{(R)-1-[6-amino-5-bromo-2-(1H-pyrazol-1-yl)pyrimidin-4-yl]pyrrolidin-2-yl}methanol
1-[6-amino-5-bromo-2-(1H-pyrazol-1-yl)pyrimidin-4-yl]azetidin-3-ol
{(S)-1-[6-amino-5-bromo-2-(1H-pyrazol-1-yl]pyrimidin-4-yl]}pyrrolidin-2-yl]methanol
1-[6-amino-5-bromo-2-(1H-pyrazol-1-yl)pyrimidin-4-yl]pyrrolidin-3-ol
5-bromo-6-((S)-3-fluoropyrrolidin-1-yl)-2-(1H-pyrazol-1-yl)pyrimidin-4-amine
5-bromo-6-[(R)-2-(methoxymethyl)pyrrolidin-1-yl]-2-(1H-pyrazol-1-yl)pyrimidin-4-amine
5-bromo-6-[(S)-3-(dimethylamino)pyrrolidin-1-yl]-2-(1H-pyrazol-1-yl)pyrimidin-4-amine
5-bromo-6-(2,5-dimethylpyrrolidin-1-yl)-2-(1H-pyrazol-1-yl)pyrimidin-4-amine
5-bromo-6-(3,3-difluoroazetidin-1-yl)-2-(1H-pyrazol-1-yl)pyrimidin-4-amine
5-bromo-N⁴-methyl-2-(1H-pyrazol-1-yl)pyrimidin-4,6-diamine
5-bromo-N⁴-ethyl-2-(1H-pyrazol-1-yl)pyrimidin-4,6-diamine
5-bromo-N⁴-(prop-2-ynyl)-2-(1H-pyrazol-1-yl)pyrimidin-4,6-diamine
5-bromo-N⁴-(2-morpholinoethyl)-2-(1H-pyrazol-1-yl)pyrimidin-4,6-diamine
5-bromo-N⁴-isopropyl-2-(1H-pyrazol-1-yl)pyrimidin-4,6-diamine
5-bromo-N⁴-(cyclopropylmethyl)-2-(1H-pyrazol-1-yl)pyrimidin-4,6-diamine
5-bromo-N⁴-propyl-2-(1H-pyrazol-1-yl)pyrimidin-4,6-diamine
5-bromo-2-(1H-pyrazol-1-yl)pyrimidin-4,6-diamine
5-chloro-2,6-di-(1H-pyrazol-1-yl)pyrimidin-4-amine
5-iodo-2,6-di(1H-pyrazol-1-yl)pyrimidin-4-amine
4-amino-2,6-di-(1H-pyrazol-1-yl)pyrimidin-5-carbonitrile
4-amino-6-N-cyclopentylamino-2-(1H-pyrazol-1-yl)pyrimidin-5-carbonitrile
5-bromo-N-methyl-2,6-di-(1H-pyrazol-1-yl)pyrimidin-4-amine
5-bromo-N-ethyl-2,6-di(1H-pyrazol-1-yl)pyrimidin-4-amine
N-benzyl-5-bromo-2,6-di(1H-pyrazol-1-yl)pyrimidin-4-amine
5-bromo-N-(prop-2-ynyl)-2,6-di(1H-pyrazol-1-yl)pyrimidin-4-amine
5-bromo-N-(2-morpholinoethyl)-2,6-di(1H-pyrazol-1-yl)pyrimidin-4-amine
5-bromo-N-[2-(piperidin-1-yl)ethyl]-2,6-di(1H-pyrazol-1-yl)pyrimidin-4-amine
5-bromo-N-cyclobutyl-2,6-di(1H-pyrazol-1-yl)pyrimidin-4-amine
N-(2-aminoethyl)-5-bromo-2,6-di(1H-pyrazol-1-yl)pyrimidin-4-amine
N⁴-tert-butyl-5-bromo-2-(1H-pyrazol-1-yl)pyrimidine-4,6-diamine
5-bromo-2-(4-methyl-1H-pyrazol-1-yl)-6-(1H-pyrazol-1-yl)pyrimidin-4-amine
6-(azetidin-1-yl)-5-bromo-2-(4-methyl-1H-pyrazol-1-yl)pyrimidin-4-amine
5-bromo-N⁴-cyclopentyl-2-(4-methyl-1H-pyrazol-1-yl)pyrimidin-4,6-diamine
5-bromo-N⁴-cyclopropyl-2-(4-methyl-1H-pyrazol-1-yl)pyrimidin-4,6-diamine
5-bromo-N⁴-cyclobutyl-2-(4-methyl-1H-pyrazol-1-yl)pyrimidin-4,6-diamine
5-bromo-2-(4-methyl-1H-pyrazol-1-yl)-6-(2-methylpyrrolidin-1-yl)pyrimidin-4-amine
5-bromo-2-(4-methyl-1H-pyrazol-1-yl)-6-((R)-2-methylpyrrolidin-1-yl)pyrimidin-4-amine
5-bromo-N-cyclopropyl-2-(4-chloro-1H-pyrazol-1-yl)pyrimidin-4,6-diamine
6-(azetidin-1-il)-5-bromo-2-(4-cloro-1H-pirazol-1-il)pirimidin-4-amina
5-bromo-2,6-di-(4-methyl-1H-pyrazol-1-yl)pyrimidin-4-amine
5-bromo-2,6-di-(4-chloro-1H-pyrazol-1-yl)pyrimidin-4-amine
5-bromo-2,6-di-(3-methyl-1H-pyrazol-1-yl)pyrimidin-4-amine
5-bromo-2,6-di-(3-trifluoromethyl-1H-pyrazol-1-yl)pyrimidin-4-amine
5-bromo-2,6-di-[5-(ethoxycarbonyl)-3-methyl-1H-pyrazol-1-yl]pyrimidin-4-amine
5-bromo-6-(3,5-dimethyl-1H-pyrazol-1-yl)-2-(1H-pyrazol-1-yl)pyrimidin-4-amine
5-bromo-6-(1H-imidazol-1-yl)-2-(1H-pyrazol-1-yl)pyrimidin-4-amine
5-bromo-6-(4-chloro-1H-pyrazol-1-yl)-2-(1H-pyrazol-1-yl)pyrimidin-4-amine
5-bromo-2-(1H-pyrazol-1-yl)-6-(2H-1,2,3-triazol-2-yl)pyrimidin-4-amine
5-bromo-2-(1H-pyrazol-1-yl)-6-(1H-1,2,4-triazol-1-yl)pyrimidin-4-amine
5-bromo-6-isopropoxy-2-(1H-pyrazol-1-yl)pyrimidin-4-amine
5-bromo-2-(4-chloro-1H-pyrazol-1-yl)-6-(1H-pyrazol-1-yl)pyrimidin-4-amine
5-bromo-2-(4-chloro-1H-pyrazol-1-yl)-6-(4-methyl-1H-pyrazol-1-yl)pyrimidin-4-amine
5-bromo-2-(3,5-dimethyl-1H-pyrazol-1-yl)-6-(1H-pyrazol-1-yl)pyrimidin-4-amine
5-bromo-N⁴-cyclopentyl-2-(3,5-dimethyl-1H-pyrazol-1-yl)pyrimidine-4,6-diamine
5-bromo-2-(3,5-dimethyl-1H-pyrazol-1-yl)-6-(pyrrolidin-1-yl)pyrimidin-4-amine
5-bromo-N⁴-isopropyl-2-(3,5-dimethyl-1H-pyrazol-1-yl)pyrimidine-4,6-diamine
5-bromo-2,6-bis(3,5-dimethyl-1H-pyrazol-1-yl)pyrimidin-4-amine
5-(1-methyl-1H-pyrazol-4-yl)-2,6-di(1H-pyrazol-1-yl)pyrimidin-4-amine
2,6-di(1H-pyrazol-1-yl)-5-(1H-pyrazol-4-yl)pyrimidin-4-amine
2,6-di(1H-pyrazol-1-yl)-5-(thiophen-2-yl)pyrimidin-4-amine
5-cyclopropyl-2,6-di(1H-pyrazol-1-yl)pyrimidin-4-amine
2,6-di(1H-pyrazol-1-yl)-5-(thiazol-2-yl)pyrimidin-4-amine
2,6-di(1H-pyrazol-1-yl)-5-(oxazol-2-yl)pyrimidin-4-amine 5-(Trifluormethyl)-2,6-di(1H-pyrazol-1-yl)pyrimidin-4-amine 5-Bromo-2,6-di(thiazol-2-yl)pyrimidin-4-amine 5-Bromo-2-(1H-pyrazol-1-yl)-6-(thiazol-2-yl)pyrimidin-4-amine 5-Bromo-6-(1H-pyrazol-1-yl)-2-(thiazol-2-yl)pyrimidin-4-amine 5-bromo-N$^4$-[1-(dimethylamino)propan-2-yl]-2-(1H-pyrazol-1-yl)pyrimidine-4,6-diamine 5-bromo-N$^4$-(1-methoxypropan-2-yl)-2-(1H-pyrazol-1-yl)pyrimidine-4,6-diamine 5-bromo-6-(1H-pyrazol-1-yl)-2-(2H-1,2,3-triazol-2-yl)pyrimidin-4-amine 5-bromo-6-ethoxy-2-(1H-pyrazol-1-yl)pyrimidin-4-amine The compounds of the present invention can be prepared by one of the processes described below. The synthetic routes are described using specific examples, which are not limiting in anyway the scope of the present invention.

Derivatives where the substituent R$^3$ is a bromine or chlorine atom can be prepared by the sequence of reactions represented in Scheme 1.

The methylthio group of the commercially available (Aldrich) derivative of formula (II) has been oxidized using 1.2 equivalents of meta-chloroperbenzoic acid at room temperature in dichloromethane (DCM) as solvent giving the sulphoxide of formula (III), which precipitates directly from the reaction.

The position 5 of the pyrimidine derivative of formula (III) has been brominated using N-bromosuccinimide in dimethylformamide (DMF) at room temperature affording the derivative of formula (IV). The analogous reaction using N-chlorosuccinimide leads to chlorinated derivatives in position 5 of pyrimidine ring are also the subject of the present invention.

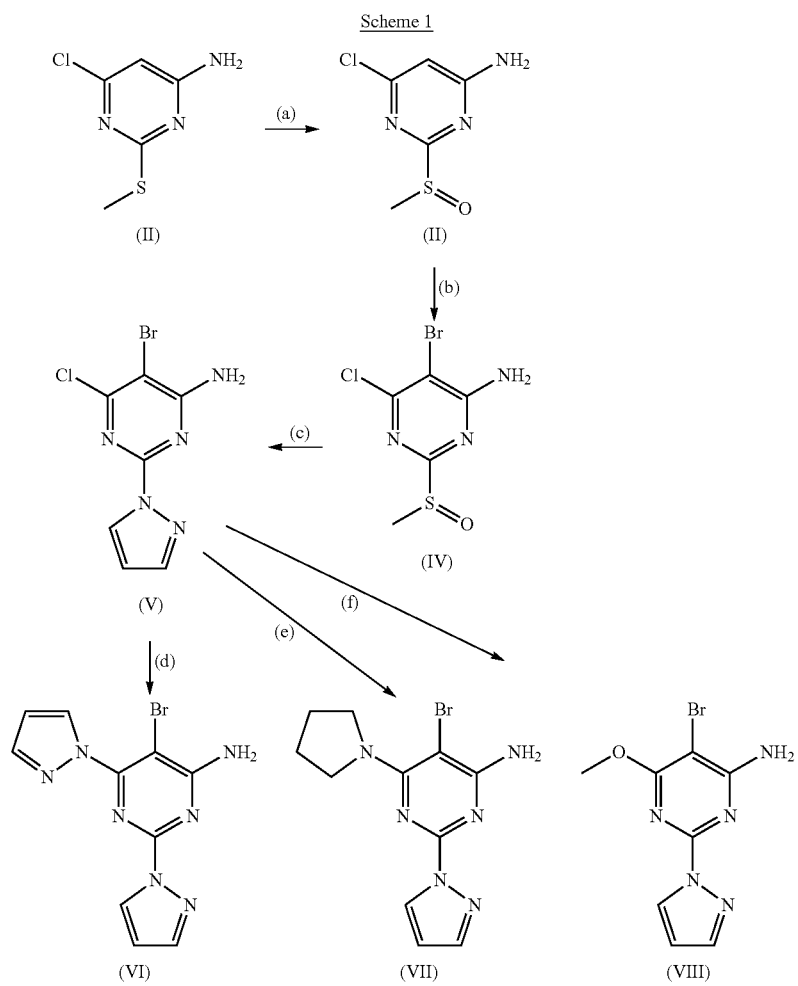

Scheme 1

Reagents and conditions: (a) m-chloroperbenzoic acid (1.2 eq), DCM, RT;
(b) N-bromosuccinimide (1.2 eq), DMF, RT; (c) pyrazole (1.3 eq), cesium carbonate, DMF, RT;
(d) 3-methylpyrazole (3 eq), cesium carbonate, DMF, 85° C.;
(e) Pyrrolidine (3 eq), THF, 60° C.; (f) Sodium methoxide, methanol, RT.

The halogenated sulphoxides of formula (IV) react with different commercially available five-membered heterocycle (e.g. pyrazoles or triazoles) derivatives at room temperature using dimethylformamide (DMF) as solvent in the presence of a base such as cesium carbonate. For example if compound of formula (IV) reacts with pyrazole under these conditions affords the derivative of formula (V).

The chlorine atom in position 6 of the pyrimidine derivative of formula (V) can be also substituted by five-membered heterocycle derivatives (e.g. pyrazoles or triazoles) using DMF as solvent and the presence of a base such as cesium carbonate at 85° C. For example, the reaction of derivative (V) with pyrazole under these conditions affords the compound of formula (VI), which is an example of the type of compounds claimed by the present invention.

Moreover pyrimidine derivatives of formula (V) may also react with primary or secondary commercially available amines, alcohols and thiols at room temperature to afford compound of formula (I) claimed by the present invention. For example reaction of derivative (V) with pyrrolidine or sodium methoxide under these conditions lead to the formation of compound of formula (VII) or (VIII), which are specific examples of compounds of formula (I) claimed in the present invention.

To synthesize pyrimidine derivatives in which the substituent $R^3$ of the 5-position of pyrimidine defined above corresponds to a cyano group or heteroaryl groups, the procedures described in Scheme 2 can be used.

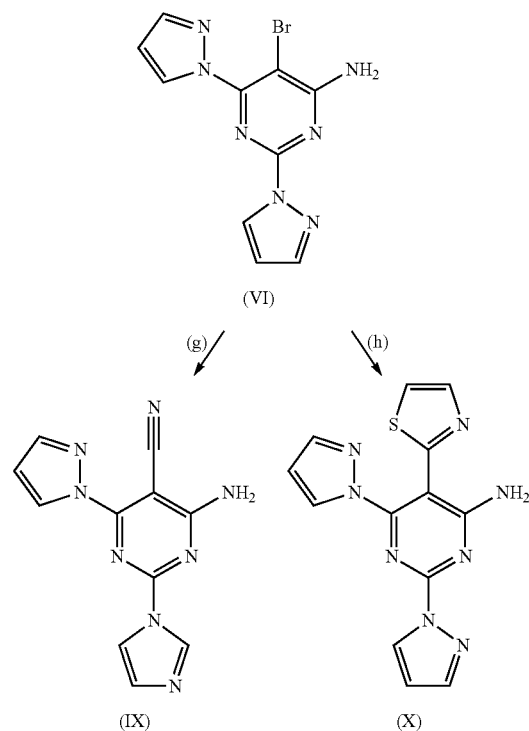

Reagents and conditions: (g) Copper (I) cyanide (1.1 eq), pyridine, microwave (MW), 20 min at 250° C.; (h) thiazolyl-2-tributylstannane, cesium carbonate, palladium catalyst, dioxane, water, MW, 20 min at 150° C..

The introduction of the cyano group is carried out using the method described by A. P. Ijzerman et al. Biorganic & Medical Chemistry 2008. For example, the reaction of bromoderivatives of formula (VII) with copper (I) cyanide under microwave conditions 20 minutes at 250° C. afforded the compound of formula (IX) containing a cyano group in position 5 of pyrimidine ring.

On the other hand, the bromo-derivative of formula (VI) reacts with commercial heteroaryl-boronic acids in a conventional Suzuki coupling reaction or with commercially available heteroaryl-tributylstannane derivatives in a conventional Stille reaction to give the derivatives where the position five of the pyrimidine ring is substituted by a heterocyclic ring. For example, reaction of compound of formula (VII) with the 2-tributylstannyl thiazole mediated by palladium catalysis yields compound of formula (X), which is a specific example of the compounds claimed in the present invention.

The compounds in which the amino group at position 4 of the pyrimidine ring is substituted by an alkyl group $R^2$ as defined above can be obtained using the synthetic route described in scheme 3.

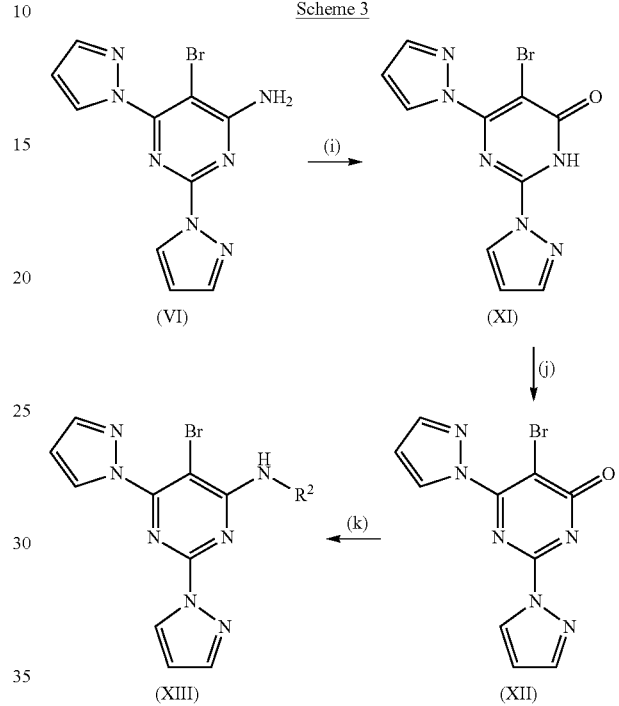

Reagents and conditions: (i) NaNO$_2$ (10 eq), AcOH, RT; (j) Thionyl chloride (2 eq), DMF/DCM, 40° C., 2 h; (k) $R^2$—NH$_2$ (3 eq), THF, RT, 24 h.

The derivative of formula (VI) reacts with sodium nitrite in acetic acid at room temperature to the respective pyrimidinone of formula (XI). The reaction of this derivative with thionyl chloride in a solution of DMF/DCM (1/2: v/v) at 40° C. leads to the formation of the 4-chloro-pyrimidine derivative of formula (XII). Compound (XII) reacts then with commercially available amines in very good yields giving the desired N-pyrimidine-4-amines of formula (XIII), which are the subject of the present invention.

If the residues $R^1$ and $R^4$, defined in the general formula (I), are the same, the derivatives can also be synthesized following the procedure described in Scheme 4.

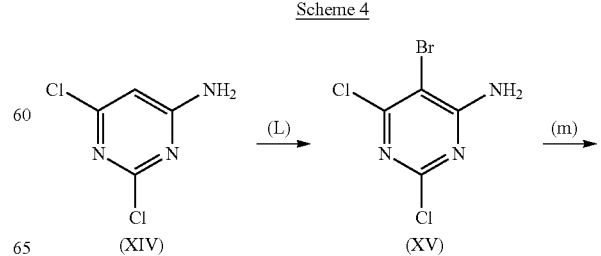

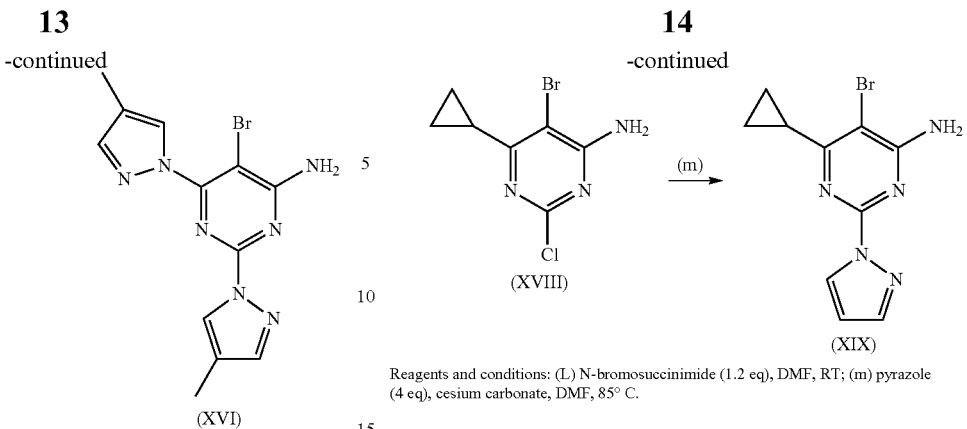

(XVI)

Reagents and conditions: (L) N-bromosuccinimide (1.2 eq), DMF, RT; (m) 4-methylpyrazole (4 eq), cesium carbonate, DMF, 85° C.

Bromination of commercially available compound of formula (XIV) is carried out with N-bromosuccinimide in DMF giving the compound of formula (XV). The reaction of compound (XIV) with different commercial pyrazoles in the presence of cesium carbonate in DMF at 85° C. leads to the formation of the pyrimidine derivatives substituted by identical pyrazole derivatives at position 2 and 6, such as compound of formula (XVI), which is an specific example of the compounds of formula (I) claimed by the present invention.

In an analogous manner, if the residue $R^4$, as defined in the general formula (I), is an alkyl or cycloalkyl group, the derivatives can also be synthesized following the procedure described in Scheme 5.

Scheme 5

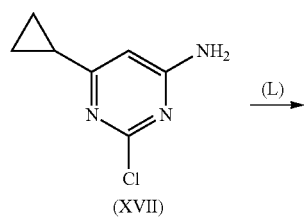

(XVII)

Reagents and conditions: (L) N-bromosuccinimide (1.2 eq), DMF, RT; (m) pyrazole (4 eq), cesium carbonate, DMF, 85° C.

Bromination of commercially available compound of formula (XVII) is carried out with N-bromosuccinimide in DMF giving the compound of formula (XVIII). The reaction of compound (XVIII) with different commercial pyrazoles in the presence of cesium carbonate in DMF at 85° C. leads to the formation of the derivatives, such as compound of formula (XIX), which is an specific example of the compounds of formula (I) claimed by the present invention.

When the substituents at position 2 and 6 of the pyrimidine ring are heterocyclic rings that can not be introduced by nucleophilic substitution, the corresponding derivatives can be synthesized as described in Scheme 6.

Commercially available derivative (XVI) reacts with commercially available pinacol esters of heteroaryl-boronic acids in a conventional Suzuki coupling reaction or with commercially available heteroaryl-tributylstannane derivatives in a conventional Stille reaction to give a mixture of all possible substitutions that can be separated by column chromatography. For example, reaction of compound of formula (XVI) with the 2-tributylstannyl thiazole mediated by palladium catalysis yields compounds of formula (XX), (XXI) and (XXII). Those intermediates can be brominated and substitute by several pyrazo derivatives giving compounds of formula (XXIII), (XIV) and (XV), which represent specific examples of the compounds of formula (I) claimed by the present invention.

Scheme 6

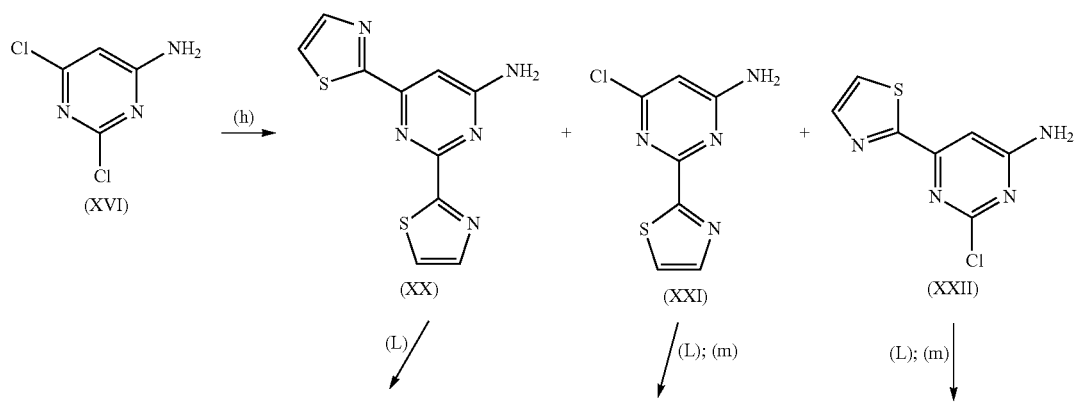

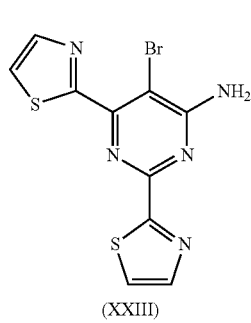 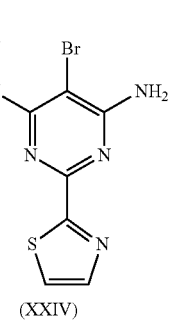 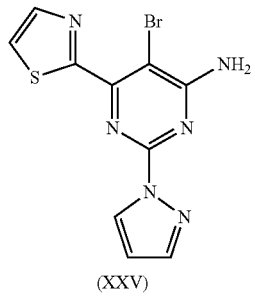

(XXIII)    (XXIV)    (XXV)

Reagents and conditions: (h) (h) thiazolyl-2-tributylstannane, cesium fluoride, palladium catalyst, dioxane, 24 h at 80° C., (L) N-bromosuccinimide (1.2 eq), DMF, RT; (m) pyrazole (4 eq), cesium carbonate, DMF, 85° C.

Pharmacological Activity

Adenosine $A_{2a}$ Receptor Subtype Competition Radioligand Binding Assay

Human membranes from recombinant adenosine receptors were purchased from Receptor Biology, Inc. (USA)

Competition assays were carried out by incubation of membranes from $hA_1$ receptors transfected to CHO cells, [$^3$H]-DPCPX as radioligand, buffer (HEPES 20 mM (pH=7.4), 10 mM $MgCl_2$, 100 mM NaCl, 2 units/ml adenosine deaminase), and unlabelled ligand in a total volume of 0.2 ml for 60 min at 25° C. R-PIA was used to determinate non-specific binding. Filter over Schleicher&Schuell GF/52 filters (pre-soaked 0.5% polyethylenimine) in a Brandel cell harvester. Unbound radioligand was removed with (3×250 μl) HEPES 20 mM (pH=7.4), 100 mM NaCl and 10 mM $MgCl_2$.

Competition assays were carried out by incubation of membranes from $hA_{2a}$ receptors transfected to HeLa cells, [$^3$H]ZM241385 as radioligand, buffer (50 mM Tris-HCl (pH=7.4), 10 mM $MgCl_2$, 1 mM EDTA, 2 units/ml adenosine deaminase), and unlabelled ligand in a total volume of 0.2 ml for 30 min at 25° C. NECA was used to determinate non-specific binding. Filter over Schleicher&Schuell GF/52 filters (pre-soaked 0.5% polyethylenimine) in a Brandel cell harvester. Unbound radioligand was removed with 3×250 μl ice-cold 50 mM Tris-HCl (pH=7.4), 10 mM MgCl and 1 mM EDTA.

Concentration-response binding competition curves were carried out by assaying 6 different concentrations (range between 10 nm to 100 μM). The inhibition constant ($K_i$) of each compound was calculated by the Cheng-Prusoff equation:

$$K_i = IC_{50}/(1+[L]/K_D)$$

where $IC_{50}$ is the concentration of compound that displaces the binding of radioligand by 50%, [L] is the free concentration of radioligand and $K_D$ is the dissociation constant of each radioligand. $IC_{50}$ values were obtained by fitting the data with non-linear regression, with Prism 2.1 software (GraphPad, San Diego, Calif.).

Cyclic Adenosine Monophosphate Production Measurement.

These assays were performed at adenosine receptors transfected using a cAMP enzymeimmunoassay kit (Amersham Biosciences). CHO-$A_{2A}$ cells were seeded (10000 cells/well) in 96-well culture plates and incubated at 37° C. in an atmosphere with 5% $CO_2$ in Dulbecco's Modified Eagle's Medium Nutrient Mixture F-12 (DMEM F-12), containing 10% Foetal Calf Serum (FCS) and 1% L-Glutamine. Cells were washed 3× with 200 μl assay medium (DMEM-F12 and 25 mM HEPES pH=7.4) and pre-incubated with assay medium containing 30 μM rolipram and test compounds at 37° C. for 15 min. 1 μM NECA was incubated for 15 min at 37° C. (total incubation time 30 min). Reaction was stopped with lysis buffer supplied in the kit and the enzymeimmunoassay was carried out for detection of intracellular cAMP at 450 nm in an Ultra Evolution detector (Tecan). Data were fitted by non-linear regression using GraphPad Prism v2.01 (GraphPad Software).

Table 1 shows the inhibition constants against the $A_{2a}$ adenosine receptor obtained in the Binding assay and in the second messenger cAMP production assay for some examples:

TABLE 1

| COMPOUND | $A_{2a}$ Binding Ki (nM) | $A_{2a}$ cAMP Ki (nM) |
|---|---|---|
| Example 1 | 12 | 25 |
| Example 3 | 11 | |
| Example 4 | 6 | |
| Example 5 | 14 | |
| Example 8 | 18 | 60 |
| Example 9 | 33 | |
| Example 10 | 21 | |
| Example 13 | 35 | 50 |
| Example 20 | 14 | |
| Example 24 | 16 | |
| Example 29 | 10 | |
| Example 36 | 8 | |
| Example 38 | 7 | |
| Example 44 | 14 | |
| Example 46 | 17 | |
| Example 48 | 7 | |
| Example 93 | 1 | 12 |

It can be seen from Table 1 that the compounds of formula (I) are potent antagonists of the adenosine $A_{2a}$ receptor.

The derivatives of the invention are useful in the treatment or prevention of diseases known to be susceptible to improvement by treatment with an antagonist of an adenosine receptor, in particular those susceptible to improvement by treatment with and antagonist of the adenosine receptor. Such diseases are, for example ischemia, supraventricular arrhythmias, atrial fibrillation acute renal failure, asthma, myocardial reperfusion injury, diseases due to fluid retention, allergic reactions including but not limited to rhinitis, urticaria, scleroderma, arthritis, other autoimmune diseases, inflammatory bowel disease, diabetes mellitus, obesity, Parkinson's disease, Huntington's disease, dystonias such as the syndrome restless leg, dyskinesias such as those caused by prolonged use of dopamine or neuroleptic drugs or sleep disorders, congestive heart failure, hypertension, intradialytic hypotension, dementia and anxiety disorders.

Accordingly, the derivatives of the invention and pharmaceutically acceptable salts thereof, and pharmaceutical compositions comprising such compound and/or salts thereof, may be used in a method of treatment of disorders of the human body which comprises administering to a subject requiring such treatment an effective amount of the pyrimidine derivative of the invention or a pharmaceutically acceptable salt thereof.

The present invention also provides pharmaceutical compositions which comprise, as an active ingredient, at least a pyrimidine derivative of formula (I) or a pharmaceutically acceptable salt thereof in association with a pharmaceutically acceptable excipient such as a carrier or diluent. The active ingredient may comprise 0.001% to 99% by weight, preferably 0.01% to 90% by weight of the composition depending upon the nature of the formulation and whether further dilution is to be made prior to application. Preferably the compositions are made up in a form suitable for oral, topical, nasal, rectal, percutaneous or injectable administration.

The pharmaceutically acceptable excipients which are admixed with the active compound or salts of such compound, to form the compositions of this invention are well-known per se and the actual excipients used depend inter alia on the intended method of administering the compositions.

Compositions of this invention are preferably adapted for injectable and per os administration. In this case, the compositions for oral administration may take the form of tablets, retard tablets, sublingual tablets, capsules, inhalation aerosols, inhalation solutions, dry powder inhalation, or liquid preparations, such as mixtures, elixirs, syrups or suspensions, all containing the compound of the invention; such preparations may be made by methods well-known in the art.

The diluents which may be used in the preparation of the compositions include those liquid and solid diluents which are compatible with the active ingredient, together with colouring or flavouring agents, if desired. Tablets or capsules may conveniently contain between 2 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form syrup. The suspensions may comprise an insoluble active compound of the invention or a pharmaceutically acceptable salt thereof in association with water, together with a suspending agent or flavouring agent.

Compositions for parenteral injection may be prepared from soluble salts, which may or may not be freeze-dried and which may be dissolved in pyrogen free aqueous media or other appropriate parenteral injection fluid.

Effective doses are normally in the range of 2-2000 mg of active ingredient per day. Daily dosage may be administered in one or more treatments, preferably from 1 to 4 treatments, per day.

The synthesis of the compounds of the invention is illustrated by the following Examples (1 to 99) including the preparation of the intermediates, which do not limit the scope of the invention in any way.

General.

Reagents, starting materials, and solvents were purchased from commercial suppliers and used as received. Concentration refers to evaporation under vacuum using a Büchi rotatory evaporator. Reaction products were purified, when necessary, by flash chromatography on silica gel (40-63 µm) with the solvent system indicated. Spectroscopic data were recorded on a Varian Gemini 200 spectrometer, Varian Gemini 300 spectrometer, Varian Inova 400 spectrometer and Brucker DPX-250 spectrometer. Melting points were recorded on a Büchi 535 apparatus. HPLC-MS were performed on a Gilson instrument equipped with a Gilson piston pump 321, a Gilson 864 vacuum degasser, a Gilson liquid handler 215, a Gilson 189 injection module, a Gilson Valvemate 7000, a 1/1000 splitter, a Gilson 307 make-up pump, a Gilson 170 diode array detector, and a Thermoquest Finnigan aQa detector. Semi-preparative purifications were carried out using a Symmetry C18 reverse phase column (100 Å, 5 □m, 19×100 mm, purchased from WATERS), and water/ammonium formiate (0.1%, pH=3) and acetonitrile/ammonium formiate (0.1%, pH=3) as mobile phase.

Intermediate 1:
6-chloro-2-(methylsulfinyl)pyrimidine-4-amine

To a stirred solution of 10.0 g (57.2 mmol) of 6-chloro-2-(methylthio)pyrimidine-4-amine in 300 ml of dichloromethane were added during 30 minutes a solution of 15.3 g (68.6 mmol) of m-chloroperbenzoic acid (77%) (Aldrich) dissolved in 200 ml of DCM. The reaction mixture was stirred at room temperature for 4 hours. The white precipitate formed was filtered, washed several times with DCM and then after drying gave 10.4 g (94.9%) of the intermediate 1.

1H-RMN (300 MHz, DMSO-$d_6$): δ=3.28 (s, 3H), 6.64 (s, 1H), 8.11 (s, 2H).

Intermediate 2: 5-bromo-6-chloro-2-(methylsulfinyl)pyrimidine-4-amine 11.2 g (62.6 mmol) de N-bromosuccinimide were slowly added to a cooled suspension of 10 g (52.2 mmol) 6-chloro-2-(methylsulfinyl)pyrimidine-4-amine in 130 ml of DMF. After 50 minutes stirring at room temperature the precipitate was filtered washed with cool DMF, several times with cool water and dried in vacuum. There was obtained 11.4 g (81%) of a white solid.

1H-RMN (300 MHz, DMSO-$d_6$): δ=2.78 (s, 3H), 8.17 (d, 2H).

Intermediate 3:
5-bromo-2,6-dichloropyrimidine-4-amine 2 g (12.2 mmol) of 4-amino-2,6-dichloropyrimidine were dissolved in 10 ml of DMF. To this solution were added 2.6 g (14.6 mmol) of N-bromosuccinimide. The reaction mixture was stirred at room temperature over night. The solution was poured onto 200 ml of cool water. The formed precipitate was filtered and washed with water. The product was obtained 2.7 g (91.9%) as a white powder.

1H-RMN (300 MHz, DMSO-$d_6$): δ=8.16 (d, 2H).

Intermediate 4: 2,5,6-trichloropyrimidine-4-amine 1 g (6.1 mmol) of 4-amino-2,6-dichloropyrimidine were dissolved in 5 ml of DMF. To this solution was added 0.98 g (7.32 mmol) of N-chlorosuccinimide. The solution was poured onto 100 ml of cool water. The formed precipitate was filtered, washed with water and dried to yield 1.4 g (80%) of a white solid.

1H-RMN (300 MHz, DMSO-$d_6$): δ=8.24 (d, 2H).

Intermediate 5: 5-bromo-6-chloro-2-(1H-pyrazol-1-yl)pyrimidine-4-amine 1 g (3.7 mmol) of 5-bromo-6-chloro-2-(methylsulfinyl)pyrimidine-4-amine (intermediate 2) was suspended in 10 ml of DMF. To this suspension were added 0.33 g (4.8 mmol) de pyrazole and 0.8 g of cesium carbonate. The reaction mixture was turned immediately light yellow color and allowed to stir at room temperature for about 1 to 2 hours. After nearly complete conversion to the corresponding monosubstituted derivative as was indicated by TLC the solution was poured onto 100 ml of cool water. The formed precipitated was filtered, washed with water and dried to afford 0.66 g (65%) of the desired product.

1H-RMN (300 MHz, DMSO-$d_6$): δ=6.56 (dd, 1H), 7.81 (d, 1H), 8.44 (d, 1H), 8.15 (d, 2H).

The following intermediates were synthesized using the procedure described for the intermediate 5 starting from the corresponding pyrazole derivatives.

Intermediate 6: 5-bromo-6-chloro-2-(4-methyl-1H-pirazol-1-yl)pyrimidine-4-amine

1H-RMN (300 MHz, DMSO-$d_6$): δ=2.08 (s, 3H), 7.63 (s, 1H), 8.21 (s, 1H), 8.17 (d, 2H).

Intermediate 7: 5-bromo-6-chloro-2-(4-chloro-1H-pyrazol-1-yl)pyrimidine-4-amine

1H-RMN (300 MHz, DMSO-$d_6$): δ=7.94 (s, 1H), 8.57 (s, 1H), 8.13 (d, 2H).

Intermediate 8: 5-bromo-2,6-di(1H-pyrazol-1-yl)pyrimidin-4(3H)-one 1.84 g (6 mmol) 5-Bromo-2,6-di-(1H-pyrazol-1-yl)pyrimidine-4-amine (example 1) were dissolved in 20 ml acetic acid. To this solution were added a solution of 4.16 g (18.4 mmol) of $NaNO_2$ in 8 ml of water in four batches over a period of five hours. The mixture was stirred at room temperature for 30 hours. The solvent was removed in vacuum and the crude residue was washed with water to yield 1.22 g (65.8%) of the pure intermediate 8.

1H-RMN (300 MHz, DMSO-$d_6$): δ=6.50 (m, 2H), 7.73 (d, 1H), 7.75 (d, 1H), 8.30 (d, 1H), 8.53 (d, 1H).

Intermediate 9: 5-bromo-4-chloro-2,6-di(1H-pyrazol-1-yl)pyrimidine

To a solution of 1 g (3.26 mmol) of 5-bromo-2,6-di(1H-pyrazol-1-yl)pyrimidin-4(3H)-one (intermediate 8) in 10 ml of DMF and 40 ml of DCM was added dropwise a solution of 0.71 ml (9.8 mmol) of thionyl chloride in 10 ml DCM. The reaction mixture was refluxed for two hours, at which time no starting material was observed by TLC. The solution was extracted two times with 10 ml of saturated solution of $NaHCO_3$ and Brine. The organic layer was separated, dried with $MgSO_4$ and concentrated to give 0.65 g (61.5%) of the 4-chloro-pyrimidine derivative.

1H-RMN (300 MHz, DMSO-$d_6$): δ=6.68 (dd, 1H), 6.73 (dd, 1H), 7.95 (d, 1H), 8.02 (d, 1H), 8.76 (d, 1H), 8.80 (d, 1H).

Intermediate 10: 2,6-dichloro-5-iodo-pyrimidine-4-amine 1 g (6.1 mmol) of 4-amino-2,6-dichloropyrimidine were dissolved in 5 ml of DMF. To this solution was added 0.76 g (7.32 mmol) of N-Iodosuccinimide. The solution was stirred 18 h at room temperature and then poured onto 100 ml of cool water. The formed precipitate was filtered, washed with water and dried to yield 1.2 g (76%) of a pale yellow solid.

1H-RMN (300 MHz, DMSO-$d_6$): δ=8.11 (d, 2H).

Intermediate 11: 2,5,6-trichloropyrimidine-4-amine

1H-RMN (300 MHz, DMSO-$d_6$): δ=8.14 (d, 2H).

Intermediate 12: 5-bromo-6-chloro-2-(3,5-dimethyl-1H-pyrazol-1-yl)pyrimidin-4-amine 1H-RMN (300 MHz, DMSO-$d_6$): δ=2.59 (s, 3H), 2.65 (s, 3H), 6.4 (s, 1H), 8.18 (d, 2H).

Intermediate 13: 5-bromo-6-chloro-2-(2H-1,2,3-triazol-2-yl)pyrimidin-4-amine

1H-RMN (300 MHz, DMSO-$d_6$): δ=7.81 (d, 1H), 8.44 (d, 1H), 8.15 (d, 2H).

EXAMPLES

Derivatives of the Intermediate 5 ($R^1$=Pyrazole)

Example 1

5-bromo-2,6-di-(1H-pyrazol-1-yl)pyrimidine-4-amine

To a solution of 0.15 g (0.55 mmol) of 5-bromo-6-chloro-2-(1H-pyrazol-1-yl)pyrimidine-4-amine (Intermediate 5) in 3 ml of DMF were added 0.11 g (1.64 mmol) of 1H-pyrazole and 0.18 g (0.55 mmol) of cesium carbonate. The mixture was stirred at 85° C. for 24 hours. The solvent DMF was concentrated under reduced pressure. The crude residue was washed with water and dried to give 0.13 g (77%) of Example 1.

1H-RMN (300 MHz, DMSO-$d_6$): δ=6.57 (dd, 1H), 6.60 (dd, 1H), 7.52 (s, 1H), 7.81 (d, 1H), 7.87 (d, 1H), 8.41 (s, 1H), 8.51 (d, 1H), 8.60 (d, 1H).

The title compound can be also synthesized from intermediate 3 using the procedure described for example 68 and pyrazole instead of 4-methyl-pyrazole The examples from 2 to 33 were synthesized using the procedure described for example 1 starting from intermediate 5 and the corresponding amines or pyrazole derivatives:

Example 2

5-bromo-6-(4-methyl-1H-pyrazol-1-yl)-2-(1H-pyrazol-1-yl)pyrimidin-4-amine

1H-RMN (300 MHz, DMSO-$d_6$): δ=2.12 (s, 3H), 6.57 (dd, 1H), 7.53 (s, 1H), 7.70 (s, 1H), 7.81 (d, 1H), 8.32 (s, 1H), 8.43 (d, 2H), 8.52 (d, 1H).

Example 3

5-bromo-2-(1H-pyrazol-1-yl)-6-(pyrrolidin-1-yl)pyrimidin-4-amine

1H-RMN (300 MHz, DMSO-$d_6$): δ=1.85 (m, 4H), 3.73 (t, 4H), 6.47 (dd, 1H), 6.85 (s, 2H), 7.69 (d, 1H), 8.45 (d, 1H).

Example 4

5-bromo-$N^4$-cyclopentyl-2-(1H-pyrazol-1-yl)pyrimidine-4,6-diamine

1H-RMN (300 MHz, DMSO-$d_6$): δ=1.55 (m, 4H), 1.70 (m, 2H), 1.96 (m, 2H), 4.40 (m, 1H), 6.26 (d, 1H), 6.48 (dd, 1H), 6.75 (s, 2H), 7.71 (d, 1H), 8.46 (d, 1H).

Example 5

5-bromo-6-(piperidin-1-yl)-2-(1H-pyrazol-1-yl)pyrimidin-4-amine

1H-RMN (300 MHz, DMSO-$d_6$): δ=1.61 (m, 6H), 3.44 (m, 4H), 6.49 (dd, 1H), 7.07 (s, 2H), 7.72 (d, 1H), 8.45 (d, 1H).

Example 6

5-bromo-6-morpholino-2-(1H-pyrazol-1-yl)pyrimidin-4-amine

1H-RMN (300 MHz, DMSO-$d_6$): δ=3.48 (t, 4H), 3.71 (t, 4H), 6.50 (dd, 1H), 7.19 (s, 2H), 7.74 (d, 1H), 8.48 (d, 1H).

Example 7

5-bromo-6-(4-methylpiperazin-1-yl)-2-(1H-pyrazol-1-yl)pyrimidin-4-amine

1H-RMN (300 MHz, DMSO-$d_6$): δ=2.21 (s, 3H), 2.43 (t, 4H), 3.49 (t, 4H), 6.50 (dd, 1H), 7.12 (s, 2H), 7.73 (d, 1H), 8.46 (d, 1H).

Example 8

5-bromo-$N^4$-cyclopropyl-2-(1H-pyrazol-1-yl)pyrimidine-4,6-diamine

1H-RMN (300 MHz, DMSO-$d_6$): δ=0.61 (m, 2H), 0.71 (m, 2H), 2.90 (m, 1H), 6.48 (dd, 1H), 6.73 (d, 1H), 6.76 (s, 2H), 7.71 (d, 1H), 8.50 (d, 1H).

Example 9

6-(azetidin-1-yl)-5-bromo-2-(1H-pyrazol-1-yl)pyrimidin-4-amine

1H-RMN (300 MHz, DMSO-$d_6$): δ=2.23 (q, 2H), 4.29 (t, 4H), 6.46 (dd, 1H), 6.87 (s, 2H), 7.70 (d, 1H), 8.42 (d, 1H).

Example 10

5-bromo-$N^4$-cyclobutyl-2-(1H-pyrazol-1-yl)pyrimidine-4,6-diamine

1H-RMN (300 MHz, CDCl$_3$): δ=1.64 (m, 2H), 2.13 (m, 2H), 2.23 (m, 2H), 4.60 (m, 1H), 6.48 (dd, 1H), 6.72 (d, 1H), 6.76 (s, 2H), 7.70 (d, 1H), 8.46 (d, 1H).

Example 11

5-bromo-6-(2-methylpyrrolidin-1-yl)-2-(1H-pyrazol-1-yl)pyrimidin-4-amine

1H-RMN (300 MHz, DMSO-$d_6$): δ=1.21 (d, 3H), 1.55 (m, 1H), 1.75 (m, 1H), 1.94 (m, 1H), 2.08 (m, 1H), 3.62 (m, 1H), 3.94 (m, 1H), 4.52 (m, 1H), 6.48 (dd, 1H), 6.88 (s, 2H), 7.71 (d, 1H), 8.42 (d, 1H).

Example 12

5-bromo-6-((R)-2-methylpyrrolidin-1-yl)-2-(1H-pyrazol-1-yl)pyrimidin-4-amine

1H-RMN (300 MHz, DMSO-$d_6$): δ=1.21 (d, 3H), 1.55 (m, 1H), 1.77 (m, 1H), 1.93 (m, 1H), 2.09 (m, 1H), 3.62 (m, 1H), 3.92 (m, 1H), 4.52 (m, 1H), 6.48 (dd, 1H), 6.88 (s, 2H), 7.71 (d, 1H), 8.42 (d, 1H).

Example 13

5-bromo-$N^4$,$N^4$-dimethyl-2-(1H-pyrazol-1-yl)pyrimidine-4,6-diamine

1H-RMN (300 MHz, DMSO-$d_6$): δ=3.09 (s, 6H), 6.49 (dd, 1H), 7.00 (s, 2H), 7.72 (d, 1H), 8.47 (d, 1H).

Example 14

5-bromo-$N^4$,$N^4$-diethyl-2-(1H-pyrazol-1-yl)pyrimidine-4,6-diamine

1H-RMN (300 MHz, DMSO-$d_6$): δ=1.19 (t, 6H), 3.55 (c, 4H), 6.49 (dd, 1H), 6.96 (s, 2H), 7.72 (d, 1H), 8.41 (d, 1H).

Example 15

((R)-1-(6-amino-5-bromo-2-(1H-pyrazol-1-yl)pyrimidin-4-yl)pyrrolidin-2-yl)methanol 1H-RMN (300 MHz, DMSO-$d_6$): δ=1.76 (m, 1H), 1.96 (m, 4H), 3.64 (m, 2H), 3.91 (m, 1H), 4.51 (m, 1H), 4.81 (t, 1H), 6.49 (dd, 1H), 6.90 (s, 2H), 7.71 (d, 1H), 8.45 (d, 1H).

Example 16

1-(6-amino-5-bromo-2-(1H-pyrazol-1-yl)pyrimidin-4-yl)azetidin-3-ol

1H-RMN (300 MHz, DMSO-$d_6$): δ=4.00 (m, 2H), 4.48 (m, 3H), 5.66 (d, 1H), 6.47 (dd, 1H), 6.90 (s, 2H), 7.70 (d, 1H), 8.43 (d, 1H).

Example 17

((S)-1-(6-amino-5-bromo-2-(1H-pyrazol-1-yl)pyrimidin-4-yl)pyrrolidin-2-yl)methanol 1H-RMN (300 MHz, DMSO-$d_6$): δ=1.87 (m, 5H), 3.62 (m, 2H), 3.91 (m, 1H), 4.52 (m, 1H), 4.83 (m, 1H), 6.49 (dd, 1H), 6.90 (s, 2H), 7.72 (d, 1H), 8.46 (d, 1H).

Example 18

1-(6-amino-5-bromo-2-(1H-pyrazol-1-yl)pyrimidin-4-yl)pyrrolidin-3-ol

1H-RMN (300 MHz, DMSO-$d_6$): δ=1.83 (m, 1H), 1.90 (m, 1H), 3.58 (m, 1H), 3.74 (m, 1H), 3.88 (m, 2H), 4.32 (m, 1H), 4.96 (d, 1H), 6.47 (dd, 1H), 6.85 (s, 2H), 7.70 (d, 1H), 8.44 (d, 1H).

Example 19

5-bromo-6-((S)-3-fluoropyrrolidin-1-yl)-2-(1H-pyrazol-1-yl)pyrimidin-4-amine

1H-RMN (300 MHz, DMSO-$d_6$): δ=2.04 (m, 1H), 2.17 (m, 1H), 3.90 (m, 3H), 4.08 (m, 1H), 5.40 (d, 1H), 6.48 (dd, 1H), 6.96 (s, 2H), 7.71 (d, 1H), 8.47 (d, 1H).

Example 20

5-bromo-6-((R)-2-(methoxymethyl)pyrrolidin-1-yl)-2-(1H-pyrazol-1-yl)pyrimidin-4-amine 1H-RMN (300 MHz, DMSO-$d_6$): δ=1.77 (m, 2H), 1.95 (m, 2H), 3.24 (s, 3H), 3.30 (m, 1H), 3.54 (m, 1H), 3.61 (m, 1H), 3.98 (m, 1H), 4.67 (m, 1H), 6.47 (dd, 1H), 6.90 (s, 2H), 7.69 (d, 1H), 8.39 (d, 1H).

Example 21

5-bromo-6-((S)-3-(dimethylamino)pyrrolidin-1-yl)-2-(1H-pyrazol-1-yl)pyrimidin-4-amine 1H-RMN (300 MHz, DMSO-$d_6$): δ=1.68 (m, 1H), 2.04 (m, 1H), 2.17 (m, 6H), 2.63 (m, 1H), 3.55 (t, 1H), 3.80 (m, 3H), 6.45 (dd, 1H), 6.86 (s, 2H), 7.68 (d, 1H), 8.43 (d, 1H).

Example 22

5-bromo-6-(2,5-dimethylpyrrolidin-1-yl)-2-(1H-pyrazol-1-yl)pyrimidin-4-amine

1H-RMN (300 MHz, DMSO-$d_6$): δ=1.34 (d, 6H), 1.72 (m, 2H), 2.00 (m, 2H), 4.65 (m, 2H), 6.48 (dd, 1H), 6.85 (s, 2H), 7.71 (d, 1H), 8.39 (d, 1H).

Example 23

5-bromo-6-(3,3-difluoroazetidin-1-yl)-2-(1H-pyrazol-1-yl)pyrimidin-4-amine

1H-RMN (300 MHz, DMSO-$d_6$): δ=4.67 (t, 4H), 6.50 (dd, 1H), 7.15 (s, 2H), 7.73 (d, 1H), 8.48 (d, 1H).

Example 24

5-bromo-$N^4$-methyl-2-(1H-pyrazol-1-yl)pyrimidine-4,6-diamine

1H-RMN (300 MHz, DMSO-$d_6$): δ=2.91 (d, 3H), 6.47 (dd, 1H), 6.70 (s, 2H), 6.75 (m, 1H), 7.70 (d, 1H), 8.49 (d, 1H).

Example 25

5-bromo-$N^4$-ethyl-2-(1H-pyrazol-1-yl)pyrimidine-4,6-diamine

1H-RMN (300 MHz, DMSO-$d_6$): δ=1.15 (t, 3H), 3.45 (m, 2H), 6.47 (dd, 1H), 6.71 (s, 2H), 6.75 (t, 1H), 7.70 (d, 1H), 8.46 (d, 1H).

Example 26

5-bromo-$N^4$-(prop-2-ynyl)-2-(1H-pyrazol-1-yl)pyrimidine-4,6-diamine

1H-RMN (300 MHz, DMSO-$d_6$): δ=3.04 (t, 1H), 4.18 (d, 2H), 6.50 (dd, 1H), 6.87 (s, 2H), 7.16 (t, 1H), 7.72 (d, 1H), 8.52 (d, 1H).

Example 27

5-bromo-$N^4$-(2-morpholinoethyl)-2-(1H-pyrazol-1-yl)pyrimidine-4,6-diamine

1H-RMN (300 MHz, DMSO-$d_6$): δ=2.44 (t, 4H), 2.52 (t, 2H), 3.52 (t, 2H), 3.56 (t, 4H), 6.48 (dd, 1H), 6.61 (t, 1H), 6.76 (s, 2H), 7.70 (d, 1H), 8.45 (d, 1H).

Example 28

5-bromo-$N^4$-isopropyl-2-(1H-pyrazol-1-yl)pyrimidine-4,6-diamine

1H-RMN (300 MHz, DMSO-$d_6$): δ=1.21 (d, 6H), 4.35 (m, 1H), 6.19 (d, 1H), 6.47 (dd, 1H), 6.74 (s, 2H), 7.70 (d, 1H), 8.45 (d, 1H).

Example 29

5-bromo-$N^4$-(cyclopropylmethyl)-2-(1H-pyrazol-1-yl)pyrimidine-4,6-diamine

1H-RMN (300 MHz, DMSO-$d_6$): δ=0.30 (m, 2H), 0.41 (m, 2H), 1.13 (m, 1H), 3.29 (t, 2H), 6.48 (dd, 1H), 6.73 (s, 2H), 6.81 (t, 1H), 7.71 (d, 1H), 8.45 (d, 1H).

Example 30

5-bromo-$N^4$-propyl-2-(1H-pyrazol-1-yl)pyrimidine-4,6-diamine

1H-RMN (300 MHz, DMSO-$d_6$): δ=0.88 (t, 3H), 1.58 (m, 2H), 3.38 (m, 2H), 6.48 (dd, 1H), 6.73 (m, 3H), 7.70 (d, 1H), 8.44 (d, 1H).

Example 31

5-bromo-$N^4$-propyl-2-(1H-pyrazol-1-yl)pyrimidine-4,6-diamine

1H-RMN (300 MHz, DMSO-$d_6$): δ=0.88 (t, 3H), 1.58 (m, 2H), 3.38 (m, 2H), 6.48 (dd, 1H), 6.73 (m, 3H), 7.70 (d, 1H), 8.44 (d, 1H).

Example 32

(R)—$N^4$-sec-butyl-5-bromo-2-(1H-pirazol-1-yl)pyrimidine-4,6-diamine

1H-RMN (300 MHz, DMSO-$d_6$): δ=0.87 (t, 3H), 1.18 (d, 3H), 1.53 (m, 1H), 1.60 (m, 1H), 4.18 (m, 1H), 6.13 (d, 1H), 6.47 (dd, 1H), 6.74 (s, 2H), 7.71 (d, 1H), 8.45 (d, 1H).

Example 33

(S)—N⁴-sec-butyl-5-bromo-2-(1H-pyrazol-1-yl)pyrimidine-4,6-diamine

1H-RMN (300 MHz, DMSO-$d_6$): δ=0.87 (t, 3H), 1.18 (d, 3H), 1.53 (m, 1H), 1.60 (m, 1H), 4.18 (m, 1H), 6.14 (d, 1H), 6.48 (dd, 1H), 6.74 (s, 2H), 7.71 (d, 8.45 (d, 1H).

Derivatives of the Intermediate 1 ($R^1$=Pyrazole, $R^4$=—S—$R^7$)

Example 34

5-bromo-6-(phenylthio)-2-(1H-pyrazol-1-yl)pyrimidin-4-amine

To a solution of 0.1 g (0.36 mmol) of 5-bromo-6-chloro-2-(1H-pyrazol-1-yl)pyrimidin-4-amine (Intermediate 5) in 4 ml of THF, 74 µl (0.73 mmol) of thiophenol and 0.178 g (0.55 mmol) of $Cs_2CO_3$ were added. The mixture was allowed to react under microwave conditions 15 min. at 100° C. Afterwards the reaction mixture was put on 10 ml of cool water. The formed white precipitate was filtered, washed several times with cold water and dried.

1H-RMN (300 MHz, DMSO-$d_6$): δ=6.40 (dd, 1H), 7.39 (t, 1H), 7.54 (m, 4H), 7.62 (m, 2H), 7.68 (m, 2H).

Example 35

5-bromo-6-(methylthio)-2-(1H-pyrazol-1-yl)pyrimidin-4-amine 0.05 g (0.73 mmol) of sodium methanethiolate was added to a solution of 0.1 g (0.36 mmol) of 5-bromo-6-chloro-2-(1H-pyrazol-1-yl)pyrimidin-4-amine (Intermediate 5) in 4 ml of THF. The mixture was stirred for 1 hour at room temperature. Then it was put on 10 ml of cool water. The formed precipitate was filtered, washed several times with cold water and dried.

1H-RMN (300 MHz, DMSO-$d_6$): δ=2.56 (s, 3H), 6.54 (dd, 1H), 7.47 (s, 2H), 7.78 (d, 1H), 8.57 (d, 1H).

Examples 36 to 38 were synthesized using the procedure described for Example 35 from Intermediate 5 using the sodium salts of the corresponding thiolates:

Example 36

5-bromo-6-(ethylthio)-2-(1H-pyrazol-1-yl)pyrimidin-4-amine

1H-RMN (300 MHz, DMSO-$d_6$): δ=1.34 (t, 3H), 3.19 (q, 2H), 6.55 (dd, 1H), 7.46 (s, 2H), 7.79 (d, 1H), 8.52 (d, 1H).

Example 37

5-bromo-6-(propylthio)-2-(1H-pyrazol-1-yl)pyrimidin-4-amine

1H-RMN (300 MHz, DMSO-$d_6$): δ=1.01 (t, 3H), 1.71 (m, 2H), 3.18 (t, 2H), 6.56 (dd, 1H), 7.47 (s, 2H), 7.79 (d, 1H), 8.51 (d, 1H).

Example 38

5-bromo-6-(isopropylthio)-2-(1H-pyrazol-1-yl)pyrimidin-4-amine

1H-RMN (300 MHz, DMSO-$d_6$): δ=1.40 (d, 6H), 4.04 (m, 1H), 6.55 (dd, 1H), 7.46 (s, 2H), 7.79 (d, 1H), 8.51 (d, 1H).

Derivative of the Intermediate 1 ($R^1$=Pyrazole, $R^4$=—O—$R^7$)

Example 39

5-bromo-6-phenoxy-2-(1H-pyrazol-1-yl)pyrimidin-4-amine

To a solution of 0.1 g (0.36 mmol) of 5-bromo-6-chloro-2-(1H-pyrazol-1-yl)pyrimidin-4-amine (Intermediate 5) in 4 ml of THF, 0.07 g (0.73 mmol) of phenol and 0.1 g (0.73 mmol) of $K_2CO_3$ were added. The mixture was allowed to react under microwave conditions 30 min. at 100° C. Afterwards the reaction mixture was put on 10 ml of cool water. The formed white precipitate was filtered, washed several times with cold water and dried.

1H-RMN (300 MHz, DMSO-$d_6$): δ=6.45 (dd, 1H), 7.26 (m, 4H), 7.46 (m, 3H), 7.70 (d, 1H), 8.06 (d, 1H).

Examples 40 to 42 were synthesized using the procedure described for Example 39 from Intermediate 5 using the corresponding aril- or heteroarilphenols:

Example 40

5-bromo-2-(1H-pyrazol-1-yl)-6-(pyridin-2-yloxy)pyrimidin-4-amine

1H-RMN (300 MHz, DMSO-$d_6$): δ=6.39 (dd, 1H), 6.55 (m, 2H), 7.58 (t, 1H), 7.69 (d, 1H), 7.80 (m, 1H), 8.03 (s, 2H), 8.47 (d, 1H).

Example 41

5-bromo-2-(1H-pyrazol-1-yl)-6-(pyridin-3-yloxy)pyrimidin-4-amine

1H-RMN (300 MHz, DMSO-$d_6$): δ=6.46 (dd, 1H), 7.33 (s, 2H), 7.52 (d, 1H), 7.71 (s, 1H), 7.77 (d, 1H), 8.07 (d, 1H), 8.51 (d, 1H), 8.56 (d, 1H).

Example 42

6-(5-chloropyridin-3-yloxy)-5-bromo-2-(1H-pyrazol-1-yl)pyrimidin-4-amine

1H-RMN (300 MHz, DMSO-$d_6$): δ=6.48 (dd, 1H), 6.37 (s, 2H), 7.73 (s, 1H), 8.11 (m, 2H), 8.58 (m, 2H).

Example 43

5-bromo-6-methoxy-2-(1H-pyrazol-1-yl)pyrimidin-4-amine 3 ml (1.5 mmol) of a solution (0.5 M) of sodium methanolate in methanol was added to a solution of 0.1 g (0.36 mmol) of 5-bromo-6-chloro-2-(1H-pyrazol-1-yl)pyrimidin-4-amine (Intermediate 5) in 4 ml of THF. The mixture was stirred for 1 hour at room temperature. Then, the solvent was removed under reduced pressure, the residue was washed several times with cold water, filtered and dried.

1H-RMN (300 MHz, DMSO-$d_6$): δ=3.99 (s, 3H), 6.54 (dd, 1H), 7.31 (s, 2H), 7.77 (d, 1H), 8.53 (d, 1H).

The following example was synthesized using the procedure described for Example 43 from Intermediate 5 using a solution of sodium 2,2,2-trifluoroethanolate in 2,2,2-trifluoroethanol:

Example 44

6-(2,2,2-trifluoroethoxy)-5-bromo-2-(1H-pyrazol-1-yl)pyrimidin-4-amine

1H-RMN (300 MHz, DMSO-$d_6$): δ=5.17 (m, 2H), 6.56 (dd, 1H), 7.33 (s, 2H), 7.79 (d, 1H), 8.64 (d, 1H).

Example 45

5-bromo-2-(1H-pyrazol-1-yl)pyrimidine-4,6-diamine

A solution of 0.10 g (0.37 mmol) of 5-bromo-6-chloro-2-(1H-pyrazol-1-yl)pyrimidine-4-amine (Intermediate 5) and 0.05 g (0.77 mmol) of sodium azide in dioxane (10 mL) was stirred at 80° C. for 6 h. The solvent was then evaporated, and the residue dissolved in methanol, Pd on charcoal added (10 mg) and hydrogenated for 30 min. The solvent was again evaporated and the residue crystallizes from ethanol.

1H-RMN (300 MHz, DMSO-$d_6$): δ=6.46 (d, 1H), 6.70 (s, 2H), 6.74 (s, 2H), 7.69 (d, 1H), 8.48 (d, 1H).

Example 46

5-chloro-2,6-di-(1H-pyrazol-1-yl)pyrimidine-4-amine 1 g (5.04 mmol) de 2,5,6-trichloropyrimidin-4-amine (Intermediate 4) was allowed to react with 2.1 g (30.2 mmol) of 1H-pyrazole and 2 g (6.05 mmol) of $Cs_2CO_3$ in 5 ml of DMF at 85° C. during 24 hours. The DMF was removed in vacuum. The crude residue was washed several times with water and then dried.

1H-RMN (300 MHz, DMSO-$d_6$): δ=6.57 (dd, 1H), 6.62 (dd, 1H), 7.70 (s, 1H), 7.81 (d, 1H), 7.90 (d, 1H), 8.36 (s, 1H), 8.59 (d, 1H), 8.63 (d, 1H).

Example 47

5-iodo-2,6-di(1H-pyrazol-1-yl)pyrimidine-4-amine

The compound has been synthesized employing the procedure described for Example 32 using intermediate 10 as starting material.

1H-RMN (300 MHz, DMSO-$d_6$): δ=6.56 (dd, 1H), 6.60 (dd, 1H), 7.55 (s, 2H), 7.79 (d, 1H), 7.87 (d, 1H), 8.74 (d, 1H), 8.75 (d, 1H).

Example 48

4-amino-2,6-di-(1H-pyrazol-1-yl)pyrimidine-5-carbonitrile

A mixture of 0.2 g (0.65 mmol) of 5-bromo-2,6-di(1H-pyrazol-1-yl)pyrimidin-4-amine and 0.06 g (0.72 mmol) of cupper (I) cyanide in 3 ml of pyridine was irradiated with microwaves at 250° C. for 20 min. After nearly complete conversion to the corresponding carbonitrile as was indicated by TLC, ethyl acetate was added and filtered throw celite. The solution was extracted two times with 10 ml of saturated solution of $NaHCO_3$ and Brine. The organic layer was separated, dried with $MgSO_4$ and concentrated to give 0.065 g (39.6%) of the desired product.

1H-RMN (300 MHz, DMSO-$d_6$): δ=6.58 (dd, 1H), 6.63 (dd, 1H), 7.72 (s, 1H), 7.81 (d, 1H), 7.89 (d, 1H), 8.39 (s, 1H), 8.55 (d, 1H), 8.61 (d, 1H).

Example 49

4-amino-6-N-cyclopentylamino-2-(1H-pyrazol-1-yl)pyrimidine-5-carbonitrile

The compound has been synthesized using the procedure described for Example 34 and 5-bromo-$N^4$-cyclopentyl-2-(1H-pyrazol-1-yl)pyrimidine-4,6-diamine (Example 4) as starting product.

1H-RMN (300 MHz, DMSO-$d_6$): δ=1.55 (m, 4H), 1.70 (m, 2H), 1.96 (m, 2H), 4.41 (m, 1H), 6.25 (d, 1H), 6.48 (dd, 1H), 6.74 (s, 2H), 7.73 (d, 1H), 8.48 (d, 1H).

Example 50

5-bromo-N-methyl-2,6-di-(1H-pyrazol-1-yl)pyrimidin-4-amine

To a solution of 0.1 g (0.31 mmol) 5-bromo-4-chloro-2,6-di(1H-pyrazol-1-yl)pyrimidine (Intermediate 9) in 3 ml of THF were added 0.124 g (1.84 mmol) of methylamine hydrochloride and 0.45 g (1.38 mmol) $Ce_2CO_3$. The reaction mixture was stirred at room temperature in a reaction tube for 48 hours. The THF was removed in vacuum and the crude product was washed with water and dried.

1H-RMN (300 MHz, DMSO-$d_6$): δ=2.89 (d, 3H), 6.58 (dd, 1H), 6.60 (dd, 1H), 7.83 (d, 1H), 7.87 (d, 1H), 7.95 (m, 1H), 8.46 (d, 1H), 8.65 (d, 1H).

The examples from 51 to 57 were synthesized using the procedure described for Example 50 from the corresponding amine and 5-bromo-4-chloro-2,6-di(1H-pyrazol-1-yl)pyrimidine (Intermediate 9) as starting product.

Example 51

5-bromo-N-ethyl-2,6-di(1H-pyrazol-1-yl)pyrimidin-4-amine

1H-RMN (300 MHz, DMSO-$d_6$): δ=1.22 (t, 3H), 3.60 (m, 2H), 6.58 (dd, 1H), 6.60 (dd, 1H), 7.83 (d, 1H), 7.87 (d, 1H), 7.95 (t, 1H), 8.46 (d, 1H), 8.65 (d, 1H).

Example 52

N-benzyl-5-bromo-2,6-di(1H-pyrazol-1-yl)pyrimidin-4-amine

1H-RMN (300 MHz, DMSO-$d_6$): δ=4.75 (d, 2H), 6.53 (dd, 1H), 6.57 (dd, 1H), 7.30 (m, 3H), 7.44 (d, 2H), 7.79 (d, 1H), 7.82 (d, 1H), 8.43 (d, 1H), 8.51 (t, 1H), 8.55 (d, 1H).

Example 53

5-bromo-N-(prop-2-ynyl)-2,6-di(1H-pyrazol-1-yl)pyrimidin-4-amine

1H-RMN (300 MHz, DMSO-$d_6$): δ=3.14 (t, 1H), 4.32 (m, 2H), 6.59 (dd, 1H), 6.61 (dd, 1H), 7.85 (d, 1H), 7.89 (d, 1H), 8.30 (t, 1H), 8.48 (d, 1H), 8.71 (d, 1H).

Example 54

5-bromo-N-(2-morpholinoethyl)-2,6-di(1H-pyrazol-1-yl)pyrimidin-4-amine

1H-RMN (300 MHz, DMSO-$d_6$): δ=2.45 (t, 4H), 2.58 (t, 2H), 3.57 (t, 2H), 3.59 (t, 4H), 6.58 (dd, 1H), 6.60 (dd, 1H), 7.68 (t, 1H), 7.83 (d, 1H), 7.87 (d, 1H), 8.48 (d, 1H), 8.65 (d, 1H).

Example 55

5-bromo-N-[2-(piperidin-1-yl)ethyl]-2,6-di(1H-pyrazol-1-yl)pyrimidin-4-amine

1H-RMN (300 MHz, DMSO-$d_6$): δ=1.37 (m, 2H), 1.48 (m, 4H), 2.44 (m, 4H), 2.58 (t, 2H), 3.60 (m, 2H), 6.58 (dd, 1H), 6.60 (dd, 1H), 7.66 (t, 1H), 7.83 (d, 1H), 7.87 (d, 1H), 8.48 (d, 1H), 8.65 (d, 1H).

Example 56

5-bromo-N-cyclobutyl-2,6-di(1H-pyrazol-1-yl)pyrimidin-4-amine

1H-RMN (300 MHz, $CDCl_3$): δ=1.86 (m, 2H), 2.04 (m, 2H), 2.54 (m, 2H), 4.75 (m, 1H), 6.22 (d, 1H), 6.46 (dd, 1H), 6.48 (dd, 1H), 7.81 (d, 1H), 7.82 (d, 1H), 8.42 (d, 1H), 8.53 (d, 1H).

Example 57

N-(2-aminoethyl)-5-bromo-2,6-di(1H-pyrazol-1-yl)pyrimidin-4-amine

1H-RMN (300 MHz, DMSO-$d_6$): δ=1.22 (t, 3H), 3.60 (m, 2H), 6.58 (dd, 1H), 6.60 (dd, 1H), 7.83 (d, 1H), 7.87 (d, 1H), 7.95 (t, 1H), 8.46 (d, 1H), 8.65 (d, 1H).

Example 58

$N^4$-tert-butyl-5-bromo-2-(1H-pyrazol-1-yl)pyrimidine-4,6-diamine

1H-RMN (300 MHz, DMSO-$d_6$): δ=1.46 (s, 9H), 5.43 (s, 1H), 6.48 (dd, 1H), 6.76 (s, 2H), 7.71 (d, 1H), 8.37 (d, 1H).

Derivative of Intermediate 6
($R^1$=4-Methyl-Pyrazole)

The examples from 59 to 65 were synthesized using the procedure described for example 1 starting from intermediate 6 and the corresponding amines or pyrazole derivatives:

Example 59

5-bromo-2-(4-methyl-1H-pyrazol-1-yl)-6-(1H-pyrazol-1-yl)pyrimidin-4-amine

1H-RMN (300 MHz, DMSO-$d_6$): δ=2.09 (s, 3H), 6.60 (dd, 1H), 7.50 (s, 1H), 7.63 (s, 1H), 7.87 (d, 1H), 8.36 (s, 1H), 8.38 (s, 1H), 8.60 (d, 1H).

Example 60

6-(azetidin-1-yl)-5-bromo-2-(4-methyl-1H-pyrazol-1-yl)pyrimidin-4-amine

1H-RMN (300 MHz, DMSO-$d_6$): δ=2.06 (s, 3H), 2.23 (m, 2H), 4.28 (t, 4H), 6.81 (s, 2H), 7.51 (s, 1H), 8.19 (s, 1H).

Example 61

5-bromo-$N^4$-cyclopentyl-2-(4-methyl-1H-pyrazol-1-yl)pyrimidine-4,6-diamine

1H-RMN (300 MHz, DMSO-$d_6$): δ=1.55 (m, 4H), 1.70 (m, 2H), 1.96 (m, 2H), 2.08 (s, 3H), 4.40 (m, 1H), 6.19 (d, 1H), 6.69 (s, 2H), 7.52 (s, 1H), 8.23 (s, 1H).

Example 62

5-bromo-$N^4$-cyclopropyl-2-(4-methyl-1H-pyrazol-1-yl)pyrimidine-4,6-diamine

1H-RMN (300 MHz, DMSO-$d_6$): δ=0.62 (m, 2H), 0.72 (m, 2H), 2.08 (s, 3H), 2.91 (m, 1H), 6.18 (d, 1H), 6.68 (s, 2H), 7.51 (s, 1H), 8.22 (s, 1H).

Example 63

5-bromo-$N^4$-cyclobutyl-2-(4-methyl-1H-pyrazol-1-yl)pyrimidine-4,6-diamine

1H-RMN (300 MHz, DMSO-$d_6$): δ=1.63 (m, 2H), 1.85 (m, 2H), 2.08 (m, 2H), 2.10 (s, 3H), 4.59 (m, 1H), 6.18 (d, 1H), 6.69 (s, 2H), 7.53 (s, 1H), 8.23 (s, 1H).

Example 64

5-bromo-2-(4-methyl-1H-pyrazol-1-yl)-6-(2-methylpyrrolidin-1-yl)pyrimidin-4-amine 1H-RMN (300 MHz, DMSO-$d_6$): δ=1.20 (d, 3H), 1.56 (m, 1H), 1.75 (m, 1H), 1.94 (m, 1H), 2.07 (m, 1H), 2.09 (s, 3H), 3.62 (m, 1H), 3.94 (m, 1H), 4.52 (m, 1H), 6.80 (s, 2H), 7.52 (s, 1H), 8.20 (s, 1H).

Example 65

5-bromo-2-(4-methyl-1H-pyrazol-1-yl)-6-(R)-2-methylpyrrolidin-1-yl)pyrimidin-4-amine 1H-RMN (300 MHz, DMSO-$d_6$): δ=1.21 (d, 3H), 1.57 (m, 1H), 1.77 (m, 1H), 1.93 (m, 1H), 2.08 (m, 1H), 2.12 (s, 3H), 3.63 (m, 1H), 3.93 (m, 1H), 4.52 (m, 1H), 6.80 (s, 2H), 7.52 (s, 1H), 8.20 (s, 1H).

Derivative of Intermediate 7
($R^1$=4-CHLORO-1H-PYRAZOLE)

The examples 66 and 67 were synthesized using the procedure described for example 1 starting from intermediate 7 and the corresponding amines or pyrazole derivatives:

Example 66

5-bromo-N-cyclopropyl-2-(4-chloro-1H-pyrazol-1-yl)pyrimidin-4,6-diamine

1H-RMN (300 MHz, DMSO-$d_6$): δ=0.60 (m, 2H), 0.70 (m, 2H), 2.88 (m, 1H), 6.71 (d, 1H), 6.80 (s, 2H), 7.73 (s, 1H), 8.35 (s, 1H).

Example 67

6-(azetidin-1-il)-5-bromo-2-(4-chloro-1H-pyrazol-1-yl)pyrimidin-4-amine

1H-RMN (300 MHz, DMSO-$d_6$): δ=2.12 (q, 2H), 4.28 (t, 4H), 6.77 (s, 2H), 7.72 (s, 1H), 8.35 (s, 1H).

Derivatives Containing the Same Substituent at the Positions 2 and 6 of the Pyrimidine Ring

Example 68

5-bromo-2,6-di-(4-methyl-1H-pyrazol-1-yl)pyrimidin-4-amine 0.2 ml (2.47 mmol) of 4-methyl-1H-pyrazole and 0.4 g (1.24 mmol) of cesium carbonate were added to a solution of 0.15 g (0.62 mmol) of 5-bromo-2,6-dichloropyrimidin-4-amine (Intermediate 3) in 3 ml of DMF. The mixture was heated at 85° C. for 24 h. The DMF was concentrated in vacuum. The residue was washed with water and dried to give 0.16 g (78.7%) of a white solid.

1H-RMN (300 MHz, DMSO-$d_6$): δ=2.07 (s, 3H), 2.10 (s, 3H), 7.69 (s, 1H), 7.72 (s, 1H), 8.31 (s, 1H), 8.39 (s, 1H), 8.16 (d, 2H).

The following derivatives were synthesized by the method used for Example 68 using the derivative of the corresponding pyrazole:

Example 69

5-bromo-2,6-di-(4-chloro-1H-pyrazol-1-yl)pyrimidin-4-amine

1H-RMN (300 MHz, DMSO-$d_6$): δ=7.71 (s, 1H), 7.74 (s, 1H), 8.36 (s, 1H), 8.41 (d, 1H), 8.16 (d, 2H).

Example 70

5-bromo-2,6-di-(3-methyl-1H-pyrazol-1-yl)pyrimidin-4-amine

1H-RMN (300 MHz, DMSO-$d_6$): δ=2.08 (t, 3H), 2.11 (t, 3H), 6.54 (d, 1H), 6.60 (d, 1H), 7.62 (d, 1H), 7.68 (d, 1H), 7.40 (d, 2H).

Example 71

5-bromo-2,6-di-(3-trifluoromethyl-1H-pyrazol-1-yl)pyrimidin-4-amine

1H-RMN (300 MHz, DMSO-$d_6$): δ=6.49 (d, 1H), 6.56 (d, 1H), 7.60 (d, 1H), 7.65 (d, 1H), 7.35 (d, 2H).

Example 72

5-bromo-2,6-di-[5-(ethoxycarbonyl)-3-methyl-1H-pyrazol-1-yl]pyrimidin-4-amine

1H-RMN (300 MHz, DMSO-$d_6$): δ=1.25 (m, 6H), 4.24 (m, 4H), 2.02 (s, 3H), 2.08 (s, 3H), 6.49 (d, 1H), 6.54 (d, 1H), 7.38 (d, 2H).

The following example was synthesized using the procedure described for Example 1 from Intermediate 5 using the corresponding amines or pyrazole derivatives:

Example 73

5-bromo-6-(3,5-dimethyl-1H-pyrazol-1-yl)-2-(1H-pyrazol-1-yl)pyrimidin-4-amine

1H-RMN (300 MHz, DMSO-$d_6$): δ=2.11 (s, 6H), 6.04 (s, 1H), 6.58 (dd, 1H), 7.54 (s, 1H), 7.82 (d, 1H), 8.42 (s, 1H), 8.53 (d, 1H).

Example 74

5-bromo-6-(1H-imidazol-1-yl)-2-(1H-pyrazol-1-yl)pyrimidin-4-amine

1H-RMN (300 MHz, DMSO-$d_6$): δ=6.57 (dd, 1H), 7.40 (d, 1H), 7.52 (s, 1H), 7.81 (d, 1H), 7.85 (d, 1H), 8.41 (s, 1H), 8.31 (s, 1H), 8.51 (d, 1H).

Example 75

5-bromo-6-(4-chloro-1H-pyrazol-1-yl)-2-(1H-pyrazol-1-yl)pyrimidin-4-amine

1H-RMN (300 MHz, DMSO-$d_6$): δ=6.57 (dd, 1H), 7.51 (s, 1H), 7.65 (s, 1H), 7.81 (d, 1H), 8.26 (s, 1H), 8.41 (s, 1H), 8.52 (d, 1H).

Example 76

5-bromo-2-(1H-pyrazol-1-yl)-6-(2H-1,2,3-triazol-2-yl)pyrimidin-4-amine

1H-RMN (300 MHz, DMSO-$d_6$): δ=6.58 (dd, 1H), 7.55 (s, 1H), 7.96 (d, 2H), 7.81 (d, 1H), 8.41 (s, 1H), 8.54 (d, 1H).

Example 77

5-bromo-2-(1H-pyrazol-1-yl)-6-(1H-1,2,4-triazol-1-yl)pyrimidin-4-amine

1H-RMN (300 MHz, DMSO-$d_6$): δ=6.58 (dd, 1H), 7.55 (s, 1H), 7.81 (d, 1H), 8.41 (s, 1H), 8.46 (s, 1H), 8.54 (d, 1H), 8.66 (s, 1H).

Example 78

5-bromo-6-isopropoxy-2-(1H-pyrazol-1-yl)pyrimidin-4-amine

1H-RMN (300 MHz, DMSO-$d_6$): δ=1.32 (d, 6H), 5.36 (m, 1H), 6.52 (dd, 1H), 7.31 (s, 2H), 7.74 (d, 1H), 8.52 (d, 1H).

Example 79

5-bromo-2-(4-chloro-1H-pyrazol-1-yl)-6-(1H-pyrazol-1-yl)pyrimidin-4-amine

1H-RMN (300 MHz, DMSO-$d_6$): δ=6.61 (dd, 1H), 7.50 (s, 1H), 7.58 (s, 1H), 7.89 (d, 1H), 8.26 (s, 1H), 8.38 (s, 1H), 8.62 (d, 1H).

Example 80

5-bromo-2-(4-chloro-1H-pyrazol-1-yl)-6-(4-methyl-1H-pyrazol-1-yl)pyrimidin-4-amine 1H-RMN (300 MHz, DMSO-$d_6$): δ=2.06 (s, 3H), 7.36 (s, 2H), 7.59 (s, 1H), 7.66 (s, 1H), 8.27 (s, 1H), 8.34 (s, 1H).

Example 81

5-bromo-2-(3,5-dimethyl-1H-pyrazol-1-yl)-6-(1H-pyrazol-1-yl)pyrimidin-4-amine 1H-RMN (300 MHz, DMSO-$d_6$): δ=2.08 (s, 6H), 6.01 (s, 1H), 6.60 (dd, 1H), 7.52 (s, 1H), 7.88 (d, 1H), 8.40 (s, 1H), 8.61 (d, 1H).

Example 82

5-bromo-$N^4$-cyclopentyl-2-(3,5-dimethyl-1H-pyrazol-1-yl)pyrimidine-4,6-diamine 1H-RMN (300 MHz, DMSO-$d_6$): δ=1.55 (m, 4H), 1.70 (m, 2H), 1.96 (m, 2H), 2.06 (s, 6H), 4.40 (m, 1H), 6.01 (s, 1H), 6.25 (d, 1H), 6.73 (s, 2H).

Example 83

5-bromo-2-(3,5-dimethyl-1H-pyrazol-1-yl)-6-(pyrrolidin-1-yl)pyrimidin-4-amine 1H-RMN (300 MHz, DMSO-$d_6$): δ=1.86 (m, 4H), 2.06 (s, 6H), 3.73 (t, 4H), 6.02 (s, 1H), 6.83 (s, 2H).

Example 84

5-bromo-$N^4$-isopropyl-2-(3,5-dimethyl-1H-pyrazol-1-yl)pyrimidine-4,6-diamine 1H-RMN (300 MHz, DMSO-$d_6$): δ=1.16 (d, 6H), 2.08 (s, 6H), 4.23 (m, 1H), 6.00 (s, 1H), 6.12 (d, 1H), 6.72 (s, 2H).

The following derivative was synthesized by the method used for Example 68 using the 3,5-Dimethyl-1H-pyrazole as starting material:

Example 85

5-bromo-2,6-bis(3,5-dimethyl-1H-pyrazol-1-yl)pyrimidin-4-amine

1H-RMN (300 MHz, DMSO-$d_6$): δ=2.06 (s, 6H), 2.11 (s, 6H), 6.02 (s, 1H), 6.05 (s, 1H), 7.49 (s, 1H), 8.39 (s, 1H).

Derivatives Containing a Heterocyclic Ring at the Positions 5 ($R^3$) of the Pyrimidine Ring

Example 86

5-(1-methyl-1H-pyrazol-4-yl)-2,6-di(1H-pyrazol-1-yl)pyrimidin-4-amine

A mixture of 0.1 g (0.33 mmol) of 5-bromo-2,6-di(1H-pyrazol-1-yl)pyrimidin-4-amine (Example 1), 0.10 g (0.49 mmol) of 1-methylpyrazole-4-boronic acid pinacol ester, 0.23 (0.72 mmol) of cesium carbonate and 5 mg (6.5 μmol) of [1,1'-Bis(diphenylphosphino) ferrocene]dichloropaladium (II) dichloromethane complex in 3 ml dioxane and 0.5 ml of water were irradiated with microwaves at 140° C. for 30 min. After cooling to room temperature ethyl acetate was added and filtered by celite. The solution was extracted two times with 10 ml of saturated solution of NaHCO$_3$ and Brine. The organic layer was separated, dried with MgSO$_4$ and concentrated. The residue was purified by column chromatography with silica gel and methylene chloride and methanol as eluent to give 45.5 mg (45.3%) of the desired product.

1H-RMN (300 MHz, DMSO-$d_6$): δ=4.05 (s, 3H), 6.56 (dd, 1H), 6.59 (dd, 1H), 7.25 (s, 1H), 7.45 (s, 1H), 7.52 (s, 1H), 7.80 (d, 1H), 7.86 (d, 1H), 8.40 (s, 1H), 8.51 (d, 1H), 8.59 (d, 1H).

The following derivative was synthesized by the method used for Example 86 using the corresponding boronic acid pinacol ester:

Example 87

2,6-di(1H-pyrazol-1-yl)-5-(1H-pyrazol-4-yl)pyrimidin-4-amine

1H-RMN (300 MHz, DMSO-$d_6$): δ=6.56 (dd, 1H), 6.60 (dd, 1H), 7.28 (d, 1H), 7.48 (s, 1H), 7.52 (s, 1H), 7.80 (d, 1H), 7.86 (d, 1H), 8.40 (s, 1H), 8.51 (d, 1H), 8.60 (d, 1H), 13.55 (d, 1H).

Example 88

2,6-di(1H-pyrazol-1-yl)-5-(thiophen-2-yl)pyrimidin-4-amine

1H-RMN (300 MHz, DMSO-$d_6$): δ=6.57 (dd, 1H), 6.60 (dd, 1H), 6.58 (dd, 1H), 7.02 (d, 1H), 7.18 (d, 1H), 7.53 (s, 1H), 7.80 (d, 1H), 7.86 (d, 1H), 8.41 (s, 1H), 8.51 (d, 1H), 8.60 (d, 1H).

Example 89

5-cyclopropyl-2,6-di(1H-pyrazol-1-yl)pyrimidin-4-amine

1H-RMN (300 MHz, DMSO-$d_6$): δ=0.41 (m, 2H), 0.65 (m, 2H), 1.61 (m, 1H), 6.57 (dd, 1H), 6.61 (dd, 1H), 7.54 (s, 1H), 7.81 (d, 1H), 7.88 (d, 1H), 8.42 (s, 1H), 8.51 (d, 1H), 8.60 (d, 1H).

Example 90

2,6-di(1H-pyrazol-1-yl)-5-(thiazol-2-yl)pyrimidin-4-amine

The reaction was carried out according to the method described by Morgan in Chem. Eur. J. 2010, 16, 4279-4283.

A mixture of 8.9 mg (13.1 µmol) of Pd-PEPPSI-IPr-catalyst, 0.1 g (0.33 mmol) of 5-bromo-2,6-di(1H-pyrazol-1-yl)pyrimidin-4-amine (Example 1), 0.1 g (0.65 mmol) of cesium fluoride and activated, crushed 4 Å molecular sieves (33 mg) in a glass vial was purged with argon and 1 ml of dioxane was added. 0.15 (0.39 mmol) of 2-tributylstannylthiazole was then added and the reaction was stirred at 80° C. for 24 h. The mixture was filtered throw celite/CsF. The solvent was removed in vacuum. The residue was purified by column chromatography with silica gel and methylene chloride and methanol as eluent to give 47.9 mg (47.2%) of the desired product.

1H-RMN (300 MHz, DMSO-$d_6$): δ=6.57 (dd, 1H), 6.58 (dd, 1H), 7.34 (d, 1H), 7.52 (s, 1H), 7.81 (d, 1H), 7.86 (d, 1H), 7.92 (d, 1H), 8.41 (s, 1H), 8.51 (d, 1H), 8.60 (d, 1H).

The following derivative was synthesized by the method used for Example 90 using 2-tributylstannyloxazole:

Example 91

5-(oxazol-2-yl)-2,6-di(1H-pyrazol-1-yl)pyrimidin-4-amine

1H-RMN (300 MHz, DMSO-$d_6$): δ=6.57 (dd, 1H), 6.56 (dd, 1H), 7.28 (d, 1H), 7.51 (s, 1H), 7.81 (d, 1H), 7.85 (d, 1H), 7.90 (d, 1H), 8.40 (s, 1H), 8.50 (d, 1H), 8.58 (d, 1H).

Example 92

5-(Trifluormethyl)-2,6-di(1H-pyrazol-1-yl)pyrimidin-4-amine

The reaction was carried out according to the method described by Buchwald in Science 2010, 328, 1679-1681.

A solution of 11.3 mg (20 mop Pd(dba)$_2$ and 15.8 mg (29.4 mop 2-(Dicyclohexylphosphino) 3,6-dimethoxy-2',4',6'-triisopropyl-1,1'-biphenyl in 3 ml of dioxane was added to a mixture of 0.1 g (0.33 mmol) of 5-bromo-2,6-di(1H-pyrazol-1-yl)pyrimidin-4-amine (Example 1), 0.04 g (0.65 mmol) of potassium fluoride. 0.093 g (0.65 mmol) of trimethyl(trifluoromethyl)silane was then added and the reaction was stirred at 140° C. for 20 h. The mixture was filtered by celite and concentrated in vacuum. The residue was purified by column chromatography with silica gel and methylene chloride and methanol as eluent to give 41.6 mg (43.1%) of the desired product.

1H-RMN (300 MHz, DMSO-$d_6$): δ=6.55 (dd, 1H), 6.58 (dd, 1H), 7.51 (s, 1H), 7.80 (d, 1H), 7.86 (d, 1H), 8.40 (s, 1H), 8.50 (d, 1H), 8.58 (d, 1H).

Derivatives Containing a Heterocyclic Ring Attached by a Carbon-Carbon Bond to the Positions 2 or 6 of the Pyrimidine Ring The intermediates from 14 to 16 were synthesized using the procedure described for example 90 starting from 2,6-dichloropyrimidin-4-amine and 2-(tributylstannyl)thiazole in a conventional Stille reaction. The three formed intermediates were separated by column chromatography with silica gel and cyclohexane and ethyl acetate as eluent:

Intermediate 14:
2-Chloro-6-(thiazol-2-yl)pyrimidin-4-amine

1H-RMN (300 MHz, DMSO-$d_6$): δ=6.80 (s, 1H), 7.50 (s, 2H), 7.64 (d, 1H), 8.09 (d, 1H).

Intermediate 15:
6-Chloro-2-(thiazol-2-yl)pyrimidin-4-amine

1H-RMN (300 MHz, DMSO-$d_6$): δ=6.78 (s, 1H), 7.49 (s, 2H), 7.56 (d, 1H), 8.04 (d, 1H).

Intermediate 16:
2,6-Di(thiazol-2-yl)pyrimidin-4-amine

1H-RMN (300 MHz, DMSO-$d_6$): δ=6.84 (s, 1H), 7.51 (s, 2H), 7.57 (d, 1H), 7.65 (d, 1H), 8.06 (d, 1H), 8.11 (d, 1H).

The following intermediates were synthesized using the procedure described for Intermediate 3 from the corresponding thiazolylpyrimidin-4-amine derivatives and N-bromosuccinimide as starting product:

Intermediate 17: 5-Bromo-2-chloro-6-(thiazol-2-yl)pyrimidin-4-amine

1H-RMN (300 MHz, DMSO-$d_6$): δ=7.41 (d, 1H), 8.01 (d, 1H), 8.16 (s, 2H).

Intermediate 18: 5-Bromo-6-chloro-2-(thiazol-2-yl)pyrimidin-4-amine

1H-RMN (300 MHz, DMSO-$d_6$): δ=7.35 (d, 1H), 7.96 (d, 1H), 8.17 (s, 2H).

Example 93

5-Bromo-2,6-di(thiazol-2-yl)pyrimidin-4-amine

The compound was synthesized following the procedure described for the synthesis Intermediate 3 using Intermediate 16 as starting product:

1H-RMN (300 MHz, DMSO-$d_6$): δ=7.35 (d, 1H), 7.41 (d, 1H), 7.96 (d, 1H), 8.01 (d, 1H), 8.18 (s, 2H).

The examples from 94 to 95 were synthesized using the procedure described for example 1 starting from the corresponding intermediate 17 and 18 and pyrazole:

Example 94

5-Bromo-2-(1H-pyrazol-1-yl)-6-(thiazol-2-yl)pyrimidin-4-amine

1H-RMN (300 MHz, DMSO-$d_6$): δ=6.57 (dd, 1H), 7.40 (d, 1H), 7.53 (s, 1H), 7.81 (d, 1H), 8.00 (d, 1H), 8.40 (s, 1H), 8.42 (d, 1H).

Example 95

5-Bromo-6-(1H-pyrazol-1-yl)-2-(thiazol-2-yl)pyrimidin-4-amine

1H-RMN (300 MHz, DMSO-$d_6$): δ=6.60 (dd, 1H), 7.36 (d, 1H), 7.51 (s, 1H), 7.87 (d, 1H), 7.97 (d, 1H), 8.42 (s, 1H), 8.60 (d, 1H).

Example 96

5-bromo-$N^4$-[1-(dimethylamino)propan-2-yl]-2-(1H-pyrazol-1-yl)pyrimidine-4,6-diamine 1H-RMN (300 MHz, DMSO-$d_6$): δ=1.18 (d, 3H), 2.15 (s, 6H), 2.20 (m, 1H), 2.43 (m, 1H), 4.27 (m, 1H), 6.18 (d, 1H), 6.46 (dd, 1H), 6.77 (s, 2H), 7.68 (d, 1H), 8.42 (d, 1H).

Example 97

5-bromo-$N^4$-(1-methoxypropan-2-yl)-2-(1H-pyrazol-1-yl)pyrimidine-4,6-diamine

1H-RMN (300 MHz, DMSO-$d_6$): δ=1.15 (d, 3H), 3.32 (s, 3H), 3.40 (d, 2H), 4.43 (m, 1H), 6.15 (d, 1H), 6.46 (dd, 1H), 6.77 (s, 2H), 7.68 (d, 1H), 8.42 (d, 1H).

Example 98

5-bromo-6-(1H-pyrazol-1-yl)-2-(2H-1,2,3-triazol-2-yl)pyrimidin-4-amine

1H-RMN (300 MHz, DMSO-$d_6$): δ=6.57 (dd, 1H), 6.60 (dd, 1H), 7.52 (s, 1H), 7.81 (d, 1H), 7.87 (d, 1H), 8.41 (s, 1H), 8.51 (d, 1H), 8.60 (d, 1H).

Example 99

5-bromo-6-ethoxy-2-(1H-pyrazol-1-yl)pyrimidin-4-amine

1H-RMN (300 MHz, DMSO-$d_6$): δ=1.29 (d, 6H), 5.29 (m, 2H), 6.54 (dd, 1H), 7.31 (s, 2H), 7.77 (d, 1H), 8.54 (d, 1H).

The invention claimed is:
1. A compound of formula (I):

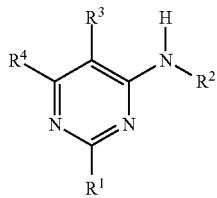

wherein
  $R^1$ represents a five-membered heteroaryl ring selected from the group consisting of a pyrazole, a thiazole, and a triazole ring optionally substituted by one or two halogen atoms or by one or two methyl groups;
  $R^2$ represents a hydrogen atom;
  $R^3$ represents bromine or chlorine atom;
  $R^4$ represents independently:
  a) a five-membered heteroaryl group optionally substituted by one or more halogen atoms or by one or more groups selected from the group consisting of alkyl, cycloalkyl, alkoxy, alkylthio, amino, mono- or dialkylamino
  b) a group —$N(R^5)(R^6)$ in which $R^5$ and $R^6$ represent independently:
  a hydrogen atom;
  an alkyl or cycloalkyl group of 3 to 6 carbon atoms, linear or branched, optionally substituted by one or more halogen atoms or by one or more groups selected from the group consisting of cycloalkyl (3-8 carbon atoms), hydroxy, alkoxy, amino, mono- and dialkylamino (1-8 carbon atoms);
  or $R^5$ and $R^6$ form together with the nitrogen atom to that they are attached a saturated heterocyclic group of 4 to 6 members in which further heteroatom may be inserted, which is optionally substituted by one or more halogen atoms or by one or more alkyl groups (1-8 carbon atoms), hydroxy, lower alkoxy, amino, mono- or dialkylamino, or
  c) a group —$OR^7$ or —$SR^7$, where $R^7$ represents independently:
  an alkyl (1-8 carbon atoms) or cycloalkyl (3-8 carbon atoms) group, linear or branched, optionally substituted by one or more halogen atoms or by one or more groups selected from the group consisting of alkyl (1-8 carbon atoms), alkoxy (1-8 carbon atoms), amino, mono- or dialkylamino (1-8 carbon atoms); or
  a Phenyl ring optionally substituted with one or more halogen atoms.

2. A compound according to claim 1 in which $R^4$ represents a pyrazole ring attached to the position 2 of the pyrimidine ring through a nitrogen atom of the pyrazole ring.

3. A compound according to claim 1 in which $R^1$ and $R^4$ represents independently a pyrazole or a thiazole ring both optionally substituted by one or two halogen atoms or by one or two methyl groups.

4. A compound according to claim 1 in which $R^1$ and $R^4$ represent a pyrazole ring optionally substituted with one or two halogen atoms or methyl groups.

5. A compound according to claim 1 in which $R^1$ represents a pyrazole or a thiazole ring optionally substituted with one or two halogen atoms or methyl groups and $R^4$ represents a group —$N(R^5)(R^6)$.

6. A compound according to claim 1 in which $R^1$ represents a pyrazole or a thiazole ring optionally substituted with one or two halogen atoms or methyl groups and $R^4$ represents a group $SR^7$ or $OR^7$, where $R^7$ represents a linear or branched alkyl group optionally substituted by fluorine atoms.

7. A compound according to claim 1 which is one of:
  5-bromo-2,6-di-(1H-pyrazol-1-yl)pyrimidin-4-amine
  5-bromo-6-(4-methyl-1H-pyrazol-1-yl)-2-(1H-pyrazol-1-yl)pyrimidin-4-amine
  5-bromo-2-(1H-pyrazol-1-yl)-6-(pyrrolidin-1-yl)pyrimidin-4-amine
  5-bromo-$N^4$-cyclopentyl-2-(1H-pyrazol-1-yl)pyrimidin-4,6-diamine
  5-bromo-6-(piperidin-1-yl)-2-(1H-pyrazol-1-yl)pyrimidin-4-amine
  5-bromo-6-morpholino-2-(1H-pyrazol-1-yl)pyrimidin-4-amine
  5-bromo-6-(4-methylpiperazin-1-yl)-2-(1H-pyrazol-1-yl)pyrimidin-4-amine
  5-bromo-$N^4$-cyclopropyl-2-(1H-pyrazol-1-yl)pyrimidine-4,6-diamine
  6-(azetidin-1-yl)-5-bromo-2-(1H-pyrazol-1-yl)pyrimidin-4-amine
  5-bromo-$N^4$-cyclobutyl-2-(1H-pyrazol-1-yl)pyrimidine-4,6-diamine
  5-bromo-6-(2-methylpyrrolidin-1-yl)-2-(1H-pyrazol-1-yl)pyrimidin-4-amine
  5-bromo-6-((R)-2-methylpyrrolidin-1-yl)-2-(1H-pyrazol-1-yl)pyrimidin-4-amine
  1-[6-amino-5-bromo-2-(1H-pyrazol-1-yl)pyrimidin-4-yl]azetidin-3-ol
  1-[6-amino-5-bromo-2-(1H-pyrazol-1-yl)pyrimidin-4-yl]pyrrolidin-3-ol
  5-bromo-6-((S)-3-fluoropyrrolidin-1-yl)-2-(1H-pyrazol-1-yl)pyrimidin-4-amine
  5-bromo-6-[(S)-3-(dimethylamino)pyrrolidin-1-yl]-2-(1H-pyrazol-1-yl)pyrimidin-4-amine
  5-bromo-6-(2,5-dimethylpyrrolidin-1-yl)-2-(1H-pyrazol-1-yl)pyrimidin-4-amine
  5-bromo-6-(3,3-difluoroazetidin-1-yl)-2-(1H-pyrazol-1-yl)pyrimidin-4-amine
  5-bromo-$N^4$-isopropyl-2-(1H-pyrazol-1-yl)pyrimidin-4,6-diamine 5-bromo-$N^4$-propyl-2-(1H-pyrazol-1-yl)pyrimidin-4,6-diamine
5-bromo-2-(1H-pyrazol-1-yl)pyrimidin-4,6-diamine
5-chloro-2,6-di-(1H-pyrazol-1-yl)pyrimidin-4-amine
$N^4$-tert-butyl-5-bromo-2-(1H-pyrazol-1-yl)pyrimidine-4,6-diamine
5-bromo-2-(4-methyl-1H-pyrazol-1-yl)-6-(1H-pyrazol-1-yl)pyrimidin-4-amine
6-(azetidin-1-yl)-5-bromo-2-(4-methyl-1H-pyrazol-1-yl)pyrimidin-4-amine
5-bromo-$N^4$-cyclopentyl-2-(4-methyl-1H-pyrazol-1-yl)pyrimidin-4,6-diamine
5-bromo-$N^4$-cyclopropyl-2-(4-methyl-1H-pyrazol-1-yl)pyrimidin-4,6-diamine
5-bromo-$N^4$-cyclobutyl-2-(4-methyl-1H-pyrazol-1-yl)pyrimidin-4,6-diamine
5-bromo-2-(4-methyl-1H-pyrazol-1-yl)-6-(2-methylpyrrolidin-1-yl)pyrimidin-4-amine
5-bromo-2-(4-methyl-1H-pyrazol-1-yl)-6-((R)-2-methylpyrrolidin-1-yl)pyrimidin-4-amine
5-bromo-N-cyclopropyl-2-(4-chloro-1H-pyrazol-1-yl)pyrimidin-4,6-diamine
6-(azetidin-1-yl)-5-bromo-2-(4-chloro-1H-pyrazol-1-yl)pyrimidin-4-amine
5-bromo-2,6-di-(4-methyl-1H-pyrazol-1-yl)pyrimidin-4-amine
5-bromo-2,6-di-(4-chloro-1H-pyrazol-1-yl)pyrimidin-4-amine
5-bromo-2,6-di-(3-methyl-1H-pyrazol-1-yl)pyrimidin-4-amine
5-bromo-6-(3,5-dimethyl-1H-pyrazol-1-yl)-2-(1H-pyrazol-1-yl)pyrimidin-4-amine
5-bromo-6-(1H-imidazol-1-yl)-2-(1H-pyrazol-1-yl)pyrimidin-4-amine
5-bromo-6-(4-chloro-1H-pyrazol-1-yl)-2-(1H-pyrazol-1-yl)pyrimidin-4-amine
5-bromo-2-(1H-pyrazol-1-yl)-6-(2H-1,2,3-triazol-2-yl)pyrimidin-4-amine
5-bromo-2-(1H-pyrazol-1-yl)-6-(1H-1,2,4-triazol-1-yl)pyrimidin-4-amine
5-bromo-6-isopropoxy-2-(1H-pyrazol-1-yl)pyrimidin-4-amine
5-bromo-2-(4-chloro-1H-pyrazol-1-yl)-6-(1H-pyrazol-1-yl)pyrimidin-4-amine
5-bromo-2-(4-chloro-1H-pyrazol-1-yl)-6-(4-methyl-1H-pyrazol-1-yl)pyrimidin-4-amine
5-bromo-2-(3,5-dimethyl-1H-pyrazol-1-yl)-6-(1H-pyrazol-1-yl)pyrimidin-4-amine
5-bromo-$N^4$-cyclopentyl-2-(3,5-dimethyl-1H-pyrazol-1-yl)pyrimidine-4,6-diamine
5-bromo-2-(3,5-dimethyl-1H-pyrazol-1-yl)-6-(pyrrolidin-1-yl)pyrimidin-4-amine
5-bromo-$N^4$-isopropyl-2-(3,5-dimethyl-1H-pyrazol-1-yl)pyrimidine-4,6-diamine
5-bromo-2,6-bis(3,5-dimethyl-1H-pyrazol-1-yl)pyrimidin-4-amine
5-Bromo-2,6-di(thiazol-2-yl)pyrimidin-4-amine
5-Bromo-2-(1H-pyrazol-1-yl)-6-(thiazol-2-yl)pyrimidin-4-amine
5-Bromo-6-(1H-pyrazol-1-yl)-2-(thiazol-2-yl)pyrimidin-4-amine
5-bromo-$N^4$-[1-(dimethylamino)propan-2-yl]-2-(1H-pyrazol-1-yl)pyrimidine-4,6-diamine
5-bromo-$N^4$-(1-methoxypropan-2-yl)-2-(1H-pyrazol-1-yl)pyrimidine-4,6-diamine
5-bromo-6-(1H-pyrazol-1-yl)-2-(2H-1,2,3-triazol-2-yl)pyrimidin-4-amine or
5-bromo-6-ethoxy-2-(1H-pyrazol-1-yl)pyrimidin-4-amine.

8. A pharmaceutical composition comprising a compound as defined in claim 1 with a pharmaceutically acceptable diluent or carrier.

9. A compound according to claim 1 in which $R^4$ represents a 2-thiazolyl ring.

10. A compound according to claim 1 in which $R^4$ represents a group —N($R^5$)($R^6$) as defined in claim 1.

11. A compound according to claim 10 in which $R^5$ represents a hydrogen atom and $R^6$ represents an alkyl or cycloalkyl group optionally substituted by halogen atoms, amino, alkylamino.

* * * * *